United States Patent
Shuber

(10) Patent No.: US 9,777,314 B2
(45) Date of Patent: Oct. 3, 2017

(54) ANALYSIS OF HETEROGENEOUS NUCLEIC ACID SAMPLES

(75) Inventor: Anthony P. Shuber, Mendon, MA (US)

(73) Assignee: Esoterix Genetic Laboratories, LLC, Burlington, NC (US)

( * ) Notice: Subject to any disclaimer, the term of this patent is extended or adjusted under 35 U.S.C. 154(b) by 923 days.

(21) Appl. No.: 11/912,056

(22) PCT Filed: Apr. 21, 2006

(86) PCT No.: PCT/US2006/015062
§ 371 (c)(1),
(2), (4) Date: Sep. 11, 2009

(87) PCT Pub. No.: WO2007/044071
PCT Pub. Date: Apr. 19, 2007

(65) Prior Publication Data
US 2009/0325153 A1   Dec. 31, 2009

Related U.S. Application Data

(60) Provisional application No. 60/673,436, filed on Apr. 21, 2005, provisional application No. 60/728,996, filed on Oct. 20, 2005.

(51) Int. Cl.
*C12Q 1/68*   (2006.01)

(52) U.S. Cl.
CPC .................. *C12Q 1/6834* (2013.01)

(58) Field of Classification Search
None
See application file for complete search history.

(56) References Cited

U.S. PATENT DOCUMENTS

| | | |
|---|---|---|
| 4,072,574 A | 2/1978 | Loeb et al. |
| 4,101,279 A | 7/1978 | Aslam |
| 4,309,782 A | 1/1982 | Paulin |
| 4,333,734 A | 6/1982 | Fleisher |
| 4,445,235 A | 5/1984 | Slover et al. |
| 4,535,058 A | 8/1985 | Weinberg et al. |
| 4,705,050 A | 11/1987 | Markham |
| 4,786,718 A | 11/1988 | Weinberg et al. |
| 4,857,300 A | 8/1989 | Maksem |

(Continued)

FOREIGN PATENT DOCUMENTS

| | | |
|---|---|---|
| AU | A-11325/95 | 4/1996 |
| EP | 0 063 879 A2 | 11/1982 |

(Continued)

OTHER PUBLICATIONS

Kwok. Curr Issues Mol Biol. (2003) 5: 43-60.*

(Continued)

*Primary Examiner* — Joseph G Dauner
(74) *Attorney, Agent, or Firm* — Kilpatrick Townsend & Stockton LLP

(57) ABSTRACT

Methods for capturing and characterizing low frequency nucleic acid molecules indicative of diseases such as cancer (e.g. adenomas or early stage cancers) are provided. In some aspects, a low complexity capture technique is combined with a high complexity analytical technique. In some aspects, samples may be analyzed using a digital analysis and/or a single molecule sequencing technique.

22 Claims, 8 Drawing Sheets

(56) References Cited

U.S. PATENT DOCUMENTS

| | | | | |
|---|---|---|---|---|
| 4,863,849 | A | 9/1989 | Melamede | |
| 4,871,838 | A | 10/1989 | Bos et al. | |
| 4,968,602 | A | 11/1990 | Dattagupta | |
| 4,968,603 | A | 11/1990 | Slamon et al. | |
| 4,988,617 | A | 1/1991 | Landegren et al. | |
| 5,075,217 | A | 12/1991 | Weber | |
| 5,087,617 | A | 2/1992 | Smith | |
| 5,126,239 | A | 6/1992 | Livak et al. | |
| 5,137,806 | A | 8/1992 | LeMaistre et al. | |
| 5,141,849 | A | 8/1992 | Chou | |
| 5,149,506 | A | 9/1992 | Skiba et al. | |
| 5,185,244 | A | 2/1993 | Wallace | |
| 5,196,167 | A | 3/1993 | Guadagno et al. | |
| 5,202,231 | A | 4/1993 | Drmanac et al. | |
| 5,248,671 | A | 9/1993 | Smith | |
| 5,272,057 | A | 12/1993 | Smulson et al. | |
| 5,296,349 | A | 3/1994 | Wallace | |
| 5,302,509 | A | 4/1994 | Cheeseman | |
| 5,330,892 | A | 7/1994 | Vogelstein et al. | |
| 5,331,973 | A | 7/1994 | Fiedler et al. | |
| 5,348,855 | A | 9/1994 | Dattagupta et al. | |
| 5,352,775 | A | 10/1994 | Albertsen et al. | |
| 5,362,623 | A | 11/1994 | Vogelstein et al. | |
| 5,369,004 | A | 11/1994 | Polymeropoulos et al. | |
| 5,378,602 | A | 1/1995 | Polymeropoulos et al. | |
| 5,380,645 | A | 1/1995 | Vogelstein | |
| 5,380,647 | A | 1/1995 | Bahar | |
| 5,382,510 | A | 1/1995 | Levine et al. | |
| 5,409,586 | A | 4/1995 | Kamahori et al. | |
| 5,455,166 | A | 10/1995 | Walker | |
| 5,458,761 | A | 10/1995 | Kamahori et al. | |
| 5,463,782 | A | 11/1995 | Carlson et al. | |
| 5,466,576 | A | 11/1995 | Schulz et al. | |
| 5,468,610 | A | 11/1995 | Polymeropoulos et al. | |
| 5,468,613 | A | 11/1995 | Erlich et al. | |
| 5,489,508 | A | 2/1996 | West et al. | |
| 5,492,808 | A | 2/1996 | de la Chapelle et al. | |
| 5,496,470 | A | 3/1996 | Lenhart | |
| 5,496,699 | A | 3/1996 | Sorenson | |
| 5,508,164 | A | 4/1996 | Kausch et al. | |
| 5,512,441 | A | 4/1996 | Ronai | |
| 5,514,547 | A | 5/1996 | Balazs et al. | |
| 5,527,676 | A | 6/1996 | Vogelstein et al. | |
| 5,532,108 | A | 7/1996 | Vogelstein | |
| 5,545,527 | A | 8/1996 | Stevens et al. | |
| 5,552,283 | A | 9/1996 | Diamandis et al. | |
| 5,561,041 | A | 10/1996 | Sidransky | |
| 5,569,584 | A | 10/1996 | Augenlicht | |
| 5,571,676 | A | 11/1996 | Shuber | |
| 5,578,458 | A | 11/1996 | Caskey et al. | |
| 5,589,330 | A | 12/1996 | Shuber | |
| 5,589,335 | A | 12/1996 | Kearney et al. | |
| 5,604,099 | A | 2/1997 | Erlich et al. | |
| 5,610,287 | A | 3/1997 | Nikiforov et al. | |
| 5,616,463 | A | 4/1997 | Fornace, Jr. et al. | |
| 5,627,032 | A | 5/1997 | Ulanovsky | |
| 5,633,134 | A | 5/1997 | Shuber | |
| 5,635,347 | A | 6/1997 | Link et al. | |
| 5,635,352 | A | 6/1997 | Urdea et al. | |
| 5,645,995 | A | 7/1997 | Kieback | |
| 5,648,212 | A | 7/1997 | Albertsen et al. | |
| 5,650,277 | A | 7/1997 | Navot et al. | |
| 5,650,281 | A | 7/1997 | Vogelstein | |
| 5,670,325 | A | 9/1997 | Lapidus et al. | |
| 5,683,877 | A | 11/1997 | Lu-Chang et al. | |
| 5,687,716 | A | 11/1997 | Kaufmann et al. | |
| 5,709,998 | A | 1/1998 | Kinzler et al. | |
| 5,710,028 | A | 1/1998 | Eyal et al. | |
| 5,726,019 | A | 3/1998 | Sidransky | |
| 5,741,650 | A | 4/1998 | Lapidus et al. | |
| 5,753,439 | A | 5/1998 | Smith et al. | |
| 5,759,777 | A | 6/1998 | Kearney et al. | |
| 5,798,266 | A | 8/1998 | Quay et al. | |
| 5,830,665 | A | 11/1998 | Shuber et al. | |
| 5,834,181 | A | 11/1998 | Shuber | |
| 5,834,193 | A | 11/1998 | Kozlowski et al. | |
| 5,846,710 | A | 12/1998 | Bajaj | |
| 5,856,092 | A | 1/1999 | Dale et al. | |
| 5,866,323 | A | 2/1999 | Markowitz et al. | |
| 5,885,775 | A | 3/1999 | Haff et al. | |
| 5,888,778 | A | * 3/1999 | Shuber | 435/91.1 |
| 5,888,819 | A | 3/1999 | Goelet et al. | |
| 5,910,407 | A | 6/1999 | Vogelstein et al. | |
| 5,928,870 | A | 7/1999 | Lapidus et al. | |
| 5,945,284 | A | 8/1999 | Livak et al. | |
| 5,952,178 | A | 9/1999 | Lapidus et al. | |
| 5,958,684 | A | 9/1999 | Van Leeuwen et al. | |
| 5,976,798 | A | 11/1999 | Parker et al. | |
| 5,976,842 | A | 11/1999 | Wurst | |
| 5,981,180 | A | 11/1999 | Chandler et al. | |
| 6,013,431 | A | 1/2000 | Soderlund et al. | |
| 6,017,704 | A | 1/2000 | Herman et al. | |
| 6,020,124 | A | 2/2000 | Sorenson | |
| 6,020,137 | A | 2/2000 | Lapidus et al. | |
| 6,054,266 | A | * 4/2000 | Kronick et al. | 435/6.12 |
| 6,074,827 | A | * 6/2000 | Nelson et al. | 435/6.12 |
| 6,084,091 | A | 7/2000 | Muller et al. | |
| 6,100,029 | A | 8/2000 | Lapidus et al. | |
| 6,100,040 | A | 8/2000 | Ramberg | |
| 6,107,032 | A | 8/2000 | Kilger et al. | |
| 6,107,061 | A | 8/2000 | Johnson | |
| 6,110,678 | A | 8/2000 | Weisburg et al. | |
| 6,114,114 | A | 9/2000 | Seilhamer et al. | |
| 6,130,049 | A | 10/2000 | Paul et al. | |
| 6,143,529 | A | 11/2000 | Lapidus et al. | |
| 6,146,828 | A | 11/2000 | Lapidus et al. | |
| 6,150,117 | A | 11/2000 | Zetter et al. | |
| 6,153,379 | A | 11/2000 | Caskey et al. | |
| 6,177,251 | B1 | 1/2001 | Vogelstein et al. | |
| 6,180,408 | B1 | 1/2001 | Kwok et al. | |
| 6,203,993 | B1 | 3/2001 | Shuber et al. | |
| 6,214,558 | B1 | 4/2001 | Shuber et al. | |
| 6,221,592 | B1 | 4/2001 | Schwartz et al. | |
| 6,225,092 | B1 | 5/2001 | Kilger et al. | |
| 6,228,596 | B1 | 5/2001 | Macina et al. | |
| 6,235,486 | B1 | 5/2001 | Young et al. | |
| 6,251,638 | B1 | 6/2001 | Umansky et al. | |
| 6,258,540 | B1 | 7/2001 | Lo et al. | |
| 6,265,229 | B1 | 7/2001 | Fodstad et al. | |
| 6,268,136 | B1 | * 7/2001 | Shuber et al. | 435/6 |
| 6,280,947 | B1 | 8/2001 | Shuber et al. | |
| 6,300,077 | B1 | 10/2001 | Shuber et al. | |
| 6,303,304 | B1 | 10/2001 | Shuber et al. | |
| 6,312,893 | B1 | 11/2001 | Van Ness et al. | |
| 6,351,857 | B2 | 3/2002 | Slaon, III et al. | |
| 6,355,433 | B1 | 3/2002 | Xu et al. | |
| 6,361,940 | B1 | 3/2002 | Van Ness et al. | |
| 6,395,493 | B1 | * 5/2002 | Sosnowski et al. | 435/6.12 |
| 6,406,857 | B1 | * 6/2002 | Shuber et al. | 435/6 |
| 6,415,555 | B1 | 7/2002 | Montague | |
| 6,428,964 | B1 | 8/2002 | Shuber | |
| 6,458,544 | B1 | 10/2002 | Miller | |
| 6,475,738 | B2 | 11/2002 | Shuber et al. | |
| 6,482,595 | B2 | 11/2002 | Shuber et al. | |
| 6,498,012 | B2 | 12/2002 | Laken | |
| 6,503,718 | B2 | 1/2003 | Shuber et al. | |
| 6,518,026 | B2 | 2/2003 | Hartley | |
| 6,534,273 | B2 | 3/2003 | Weisburg et al. | |
| 6,551,777 | B1 | 4/2003 | Shuber et al. | |
| 6,566,101 | B1 | 5/2003 | Shuber et al. | |
| 6,586,177 | B1 | 7/2003 | Shuber | |
| 6,605,433 | B1 | 8/2003 | Fliss et al. | |
| 6,818,404 | B2 | 11/2004 | Shuber | |
| 6,844,155 | B2 | 1/2005 | Shuber | |
| 6,919,174 | B1 | 7/2005 | Shuber | |
| 7,432,050 | B2 | 10/2008 | Markowitz | |
| 7,485,420 | B2 | 2/2009 | Markowitz | |
| 2001/0018180 | A1 | 8/2001 | Shuber et al. | |
| 2001/0039012 | A1 | 11/2001 | Lapidus | |
| 2001/0042264 | A1 | 11/2001 | Sloan et al. | |
| 2002/0001800 | A1 | 1/2002 | Lapidus | |
| 2002/0004201 | A1 | 1/2002 | Lapidus et al. | |
| 2002/0009727 | A1 | 1/2002 | Schultz et al. | |
| 2002/0012922 | A1 | 1/2002 | Hilbush et al. | |

(56) References Cited

U.S. PATENT DOCUMENTS

| | | |
|---|---|---|
| 2002/0025525 A1 | 2/2002 | Shuber |
| 2002/0040498 A1 | 4/2002 | Sloan et al. |
| 2002/0045183 A1 | 4/2002 | Shuber et al. |
| 2002/0048752 A1 | 4/2002 | Lapidus et al. |
| 2002/0064787 A1 | 5/2002 | Shuber et al. |
| 2002/0102604 A1 | 8/2002 | Milne Edwards et al. |
| 2002/0110810 A1 | 8/2002 | Shuber |
| 2002/0119469 A1 | 8/2002 | Shuber et al. |
| 2002/0119472 A1 | 8/2002 | Lapidus et al. |
| 2002/0123052 A1 | 9/2002 | Laken |
| 2002/0132244 A1* | 9/2002 | Li-Sucholeiki ............ 435/6 |
| 2002/0132251 A1 | 9/2002 | Shuber |
| 2002/0164631 A1 | 11/2002 | Shuber et al. |
| 2003/0044780 A1 | 3/2003 | Lapidus et al. |
| 2003/0049659 A1 | 3/2003 | Lapidus et al. |
| 2003/0054396 A1* | 3/2003 | Weiner ............ 435/6 |
| 2003/0087258 A1 | 5/2003 | Shuber |
| 2003/0203382 A1* | 10/2003 | Shuber et al. ............ 435/6 |
| 2005/0247563 A1* | 11/2005 | Shuber ............ G01N 27/44713 204/450 |
| 2008/0145852 A1 | 6/2008 | Shuber |

FOREIGN PATENT DOCUMENTS

| | | |
|---|---|---|
| EP | 0 185 494 A2 | 6/1986 |
| EP | 0 284 362 A2 | 9/1988 |
| EP | 0 332 435 A2 | 9/1989 |
| EP | 0 337 498 A2 | 10/1989 |
| EP | 0 063 879 B1 | 11/1989 |
| EP | 0 390 323 A2 | 10/1990 |
| EP | 0 390 323 A3 | 10/1990 |
| EP | 0 407 789 A1 | 1/1991 |
| EP | 0 407 789 B1 | 1/1991 |
| EP | 0 408 918 A1 | 1/1991 |
| EP | 0 332 435 B1 | 4/1992 |
| EP | 0 497 527 A1 | 8/1992 |
| EP | 0 408 918 B1 | 11/1993 |
| EP | 0 608 004 A2 | 7/1994 |
| EP | 0 259 031 B1 | 11/1994 |
| EP | 0 664 339 A1 | 7/1995 |
| EP | 1 251 183 A2 | 10/2002 |
| GB | 2 293 238 A | 3/1996 |
| WO | WO-89/11211 | 11/1989 |
| WO | WO-90/09455 | 8/1990 |
| WO | WO-91/02087 | 2/1991 |
| WO | WO-91/13075 | 9/1991 |
| WO | WO-92/13103 | 8/1992 |
| WO | WO-92/15712 | 9/1992 |
| WO | WO-92/16657 | 10/1992 |
| WO | WO-93/06240 | 4/1993 |
| WO | WO-93/18186 | 9/1993 |
| WO | WO-93/20233 | 10/1993 |
| WO | WO-93/20235 | 10/1993 |
| WO | WO-93/25563 | 12/1993 |
| WO | WO-94/00603 | 1/1994 |
| WO | WO-94/01447 | 1/1994 |
| WO | WO-94/09161 | 4/1994 |
| WO | WO-94/10575 | 5/1994 |
| WO | WO-94/11383 | 5/1994 |
| WO | WO-94/23055 | 10/1994 |
| WO | WO-95/00669 | 1/1995 |
| WO | WO-95/07361 | 3/1995 |
| WO | WO-95/09928 | 4/1995 |
| WO | WO-95/09929 | 4/1995 |
| WO | WO-95/12606 | 5/1995 |
| WO | WO-95/12607 | 5/1995 |
| WO | WO-95/13397 | 5/1995 |
| WO | WO-95/14108 | 5/1995 |
| WO | WO-95/15400 | 6/1995 |
| WO | WO-95/16792 | 6/1995 |
| WO | WO-95/18818 | 7/1995 |
| WO | WO-95/19448 | 7/1995 |
| WO | WO-95/20680 | 8/1995 |
| WO | WO-95/25813 | 9/1995 |
| WO | WO-95/31728 | 11/1995 |
| WO | WO-96/01907 | 1/1996 |
| WO | WO-96/02671 | 2/1996 |
| WO | WO-96/06951 | 3/1996 |
| WO | WO-96/08514 | 3/1996 |
| WO | WO-96/12821 | 5/1996 |
| WO | WO-96/13611 | 5/1996 |
| WO | WO-96/23895 A | 8/1996 |
| WO | WO-96/30545 | 10/1996 |
| WO | WO-97/09449 | 3/1997 |
| WO | WO-97/09600 | 3/1997 |
| WO | WO-97/22719 | 6/1997 |
| WO | WO-97/23651 | 7/1997 |
| WO | WO-97/25442 | 7/1997 |
| WO | WO-97/28450 | 8/1997 |
| WO | WO-98/13522 | 4/1998 |
| WO | WO-98/14616 | 4/1998 |
| WO | WO-98/38338 | 9/1998 |
| WO | WO-98/39474 | 9/1998 |
| WO | WO-98/39478 | 9/1998 |
| WO | WO-98/58081 | 12/1998 |
| WO | WO-98/58084 | 12/1998 |
| WO | WO-99/20798 | 4/1999 |
| WO | WO-99/28507 | 6/1999 |
| WO | WO-99/43851 | 9/1999 |
| WO | WO-99/45147 | 9/1999 |
| WO | WO-99/53316 | 10/1999 |
| WO | WO-99/55912 | 11/1999 |
| WO | WO-99/60160 | 11/1999 |
| WO | WO-99/60161 | 11/1999 |
| WO | WO-99/60162 | 11/1999 |
| WO | WO-99/66077 | 12/1999 |
| WO | WO-00/09751 | 2/2000 |
| WO | WO-00/11215 | 3/2000 |
| WO | WO-00/31298 | 6/2000 |
| WO | WO-00/31303 | 6/2000 |
| WO | WO-00/31305 | 6/2000 |
| WO | WO-00/32820 | 6/2000 |
| WO | WO-00/42223 | 7/2000 |
| WO | WO-00/50640 | 8/2000 |
| WO | WO 0053805 A1 * | 9/2000 |
| WO | WO-00/58514 | 10/2000 |
| WO | WO-00/61808 | 10/2000 |
| WO | WO-00/66005 | 11/2000 |
| WO | WO-00/70096 | 11/2000 |
| WO | WO-01/11083 | 2/2001 |
| WO | WO-01/18252 | 3/2001 |
| WO | WO-01/42502 | 6/2001 |
| WO | WO-01/42503 | 6/2001 |
| WO | WO-01/42781 | 6/2001 |
| WO | WO-01/64950 A2 | 9/2001 |
| WO | WO-02/055740 | 7/2002 |
| WO | WO-02/059379 | 8/2002 |
| WO | WO-02/074995 | 9/2002 |
| WO | WO-02/092858 | 11/2002 |
| WO | WO-02/099126 | 12/2002 |
| WO | WO-03/044217 | 5/2003 |
| WO | WO-03/071252 | 8/2003 |
| WO | WO-03/104427 A | 12/2003 |
| WO | WO-03/071252 A3 | 1/2004 |
| WO | WO-2004/007773 | 1/2004 |
| WO | WO-2004/113574 A | 12/2004 |
| WO | WO-2005/017207 A2 | 2/2005 |
| WO | WO-2005/111244 A3 | 4/2006 |
| WO | WO-2007/044071 A3 | 1/2008 |

OTHER PUBLICATIONS

Khrapko. Nucleic Acids Research, 1997, vol. 25, No. 4: 685-693.*

Aaltonen et al (1994) "Replication Errors in Benign and Malignant Tumors from Hereditary Nonpolyposis Colorectal Cancer Patients" Cancer Research 54:1645-1648.

Aaltonen et al (1998) "Incidence of Hereditary Nonpolyposis Colorectal Cancer and the Feasibility of Molecular Screening for the Disease" The New England Journal of Medicine 338:1481-1487.

(56) References Cited

OTHER PUBLICATIONS

Abarzua et al (1984) "Enzymatic techniques for the isolation of random single-base substitutions in vitro at high frequency" Proc. Natl. Acad. Sci., 81:2030-2034.
Agathanggelou et al. (2001) "Methylation associated inactivation of RASSF1A from region 3p21.3 in lung, breast and ovarian tumours," Oncogene 20(12):1509-18.
Agathanggelou et al. (2003) "Epigenetic inactivation of the candidate 3p21.3 suppressor gene BLU in human cancers," Oncogene 22(10):1580-8.
Agathanggelou et al. (2003) "Identification of novel gene expression targets for the Ras association domain family 1 (RASSF1A) tumor suppressor gene in non-small celllung cancer and neuroblastoma," Cancer Res. 63(17):5344-51.
Agathanggelou et al. (2005) "Role of the Ras-association domain family 1 tumor suppressor gene in human cancers," Cancer Res. 65(9):3497-508. Erratum in: Cancer Res. 65(12):5480.
Ahlquist et al (2000) "Colorectal Cancer Screening by Detection of Altered Human DNA in Stool: Feasibility of a Multitarget Assay Panel" Gastroenterology, 119:1219-1227.
Akino et al. (2005) "The Ras Effector RASSF2 is a Novel Tumor-Suppressor Gene in Human Colorectal Cancer." Gastroenterology, 129:156-169.
Alonzo et al. (2007) "Statistical methods for evaluating DNA methylation as a marker for early detection or prognosis," Disease Markers, 23:113-120.
Ausubel et al. (1995) Short Protocols in Molecular Biology, 3d ed., pp. 2-3-2-12, 3-30-3-33.
Azhikina et al (1996) "Factors affecting the priming efficiency of short contiguous oligonucleotide strings in the primer walking strategy of DNA sequencing" DNA Sequence—The Journal of Sequencing and Mapping, 6:211-216.
Beck (1987) "Colorimetric-detected DNA sequencing" Anal. Biochem., 164(2):514-520. Abstract only.
Behn et al. (1998) "Frequent detection of ras and p53 mutations in brush cytology samples from lung cancer patients by a restriction fragment length polymorphism-based "enriched PCR" technique," Clin Cancer Res. 4(2):361-71.
Behn et al. (1998) "Sensitive detection of p53 gene mutations by a 'mutant enriched' PCR-SSCP technique," Nucleic Acids Res. 26(5):1356-8.
Behn et al. (1998) "Simple and reliable factor V genotyping by PNA-mediated PCR clamping," Thromb Haemost. 79(4):773-7.
Bertario et al (1999) "Risk of Colorectal Cander Following Colonoscopic Polypectomy" Tumori, 85:157-162.
Beskin et al. (1995) "On the Mechanism of the Modular Primer Effect," Nucleic Acids Research, vol. 23, No. 15, ppo 2881-2885.
Blum H.E., (1995) "Colorectal Cancer: Future Population Screening for Early Colorectal Cancer" European Journal of Cancer, vol. 31A, pp. 1369-1372.
Bohm et al, (1997) "Deletion Analysis at the DEL-27, APC and WS] Loci in Bladder Cancer: LOH at the DEL-27 Locus on 5p13-12 is a Prognostic Marker of Tumor Progression," Int. J. of Cancer, 74, 291-295.
Boom et al. (1990) "Rapid and Simple Method for Purification of Nucleic Acids," Journal of Clinical Microbiology, vol. 28, No. 3, pp. 495-503.
Bos et al, (1987) "Prevalence of ras Gene Mutations in Human Colorectal Cancers" Nature vol. 327, pp. 293-297.
Botstein et al. (1985) "Strategiesand Applications of in vitro Mutagenesis," Science, 229(4719):1193-1201.
Boynton et al. (2003) "DNA integrity as a potential marker for stool-based detection of colorectal cancer," Clinical Chemistry, 49(7):1058-1065.
Braun et al, (1997) "Improved Analysis of Microsatellites Using Mass spectrometry" Genomics, vol. 46, pp. 18-23.
Brenner et al. (2005) "Fecal DNA Biomarkers for the Detection of Colorectal Neoplasia: Attractive, but is it feasible?" Journal of the National Cancer Institute, 97(15):1107-1109.

Brochure (undated) "Genotyping on the Tm/Luminex Universal Array Platform Using Primer Extension Chemistry," Tm Bioscience Corporation Technical Bulletin—403, six pages.
Burbee et al. (2001) "Epigenetic inactivation of RASSF1A in lung and breast cancers and malignant phenotype suppression," J Natl Cancer Inst. 93(9):691-9.
Caetano-Anolles "Amplifying DNA with Arbitrary Oligonucleotide Primers," Cold Spring Harbor Laboratory Press, ISSN 1054-9803, pp. 85-94 (1993).
Caldas et al. (1994) "Detection of K-ras Mutations in the Stool of Patients with Pancreatic Adenocarcinoma and Pancreatic Ductal Hyperplasia" Cancer Research, vol. 54, pp. 3568-3573.
Capozzi et al. (1999) Evaluation of the Replication Error Phenotype in Relation to Molecular and Clinicopaihological Features in Hereditary and Early Onset Colorectal Cancee' European Journal of Cancer 35:289-295.
Carothers et al. "Point Mutation Analysis in a Mammalian Gene: Rapid Preparation of Total RNA, PCR Amplification of cDNA, and Taq Sequencing by a Novel Method," 494 BioTechniques, vol. 7, pp. 494-499 (date unknown) Abstract only.
Cave et al. (1994) "Reliability of PCR Directly from Stool Samples: Usefulness of an Internal Standard," BioTechniques, vol. 16, No. 5, pp. 809-810.
Chambers et al. (1986) "The structure of the mouse glutathione peroxidase gene: the selenocysteine in the active site is encoded by the 'termination' codon, TGA" EMBO Journal 5(6):1221-1227. Abstract only.
Chapelle (1999) "Testing Tumors for Microsatellite Instability" European Journal of Human Genetics 7:407-408.
Charlesworth et al. (Sep. 15, 1994) "The Evolutionary Dynamics of Repetitive DNA in Eukaryotes," Nature, vol. 371, pp. 215-220.
Chen et al. (1985) "Supercoil Sequencing: A Fast and Simple Method for Sequencing Plasmid DNA" DNA, 4(2):165-170.
Chen et al. (1997) "Fluorescence Energy Transfer Detection as a Homogeneous DNA Diagnostic Method," Proc. Natl Acad. Sci., vol. 97, pp. 10756-10761.
Chen et al. (1997) "Microsatellite Instability in Sporadic-Colon-Cancer Patients With and Without Liver Metastases" International Journal of Cancer, 74:470-474.
Chen et al. (1997) "Template-Directed Dye-Terminator Incorporation (TDI) Assay: A Homogeneous DNA Diagnostic Method Based on Fluorescence Resonance Energy Transfer," Nucleic Acids. Research, vol. 25, No. 2, pp. 347-353.
Chen et al. (2005) "Detection in fecal DNA of colon cancer-specific methylation of the nonexpressed vimentin gene," J Natl Cancer Inst. 97:1124-1132.
Coughlin et al. (1999) "Public Health Perspectives on Testing for Colorectal Cancer Susceptibility Genes" American Journal of Preventive Medicine, 16:99-104.
Cunningham C. and M.G. Dunlop, (1996) "Molecular Genetic Basis of Colorectal Cancer Susceptibility," British Journal of Surgery vol. 83, pp. 321-329.
Dallol et al. (2004) "RASSF1A interacts with microtubule-associated proteins and modulates microtubule dynamics," Cancer Res. 64(12):4112-6.
Dammann et al. (2000) "Epigenetic inactivation of a RAS association domain family protein from the lung tumour suppressor locus 3p21.3."Nat Genet. 25(3):315-9.
Deng et al., (1996) "Loss of Heterozygosity in Normal Tissue Adjacent to Breast Carcinomas," Science. vol. 274, pp. 2057-2059.
Deuter et al. (1995) "A Method for Preparation of Fecal DNA Suitable for PCR," Nucleic Acids Research, vol. 23, No. 18, pp. 3800-3801.
Dib et al. (1996) "A Comprehensive Genetic Map of the Human Genome Based on 5,264 Microsatellites," Nature vol. 380, pp. 152-154.
Downward (2002) "Targeting RAS signalling pathways in cancer therapy," Nat Rev Cancer. 3(1):11-22.
Downward (2003) "Cell biology: metabolism meets death," Nature. 424(6951):896-7.
Downward (2003) "Role of receptor tyrosine kinases in G-protein-coupled receptor regulation of Ras: transactivation or parallel pathways?" Biochem J. 376(Pt 3):e9-10.

(56) References Cited

OTHER PUBLICATIONS

Dreijerink et al. (2001) "The candidate tumor suppressor gene, RASSF1A, from human chromosome 3p21.3 is involved in kidney tumorigenesis," Proc Natl Acad Sci USA, 98(13):7504-9.
Driscoll et al. (1989) "An in Vitro System for the Editing of Apolipoprotein B mRNA" Cell, 58:519-525.
Duffy (1995) "Can Molecular Markers Now be Used for Early Diagnosis of Malignancy?" Clin. Chem. vol. 41, No. 10, pp. 1410-1413.
Eckfeld et al. (2004) "RASSF4/AD037 is a potential ras effector/tumor suppressor of the RASSF family," Cancer Res. 64(23):8688-93.
Eguchi et al. (1996) "Mutations of the p53 Gene in the Stool of Patients with Resectable Colorectal Cancer," Cancer Supplement, vol. 77, No. 8, pp. 1707-1710.
Enari et al. (1998) "A Caspase-Activated DNase that Degrades DNA During Apoptosis, and its Inhibitor ICAD," Nature, vol. 391, pp. 43-50.
Endoh et al. (2005) "RASSF2, a potential tumor suppressor, is silenced by CpG island hypermethylation in gastric cancer," British Journal of Cancer, 93:1395-1399.
England et al. (1978) "3'-Terminal labeling of RNA with T4 RNA ligase," Nature 275:560-561.
Erickson et al. (2001) "One base sequencing (OBS): an improved method for accurate SNP scoring," Human Genome Meeting (HGM).
Erster et al, (1988) "Use of Rnase H and primer extension to analyze RNA splicing," Nucleic Acids Res., 16(13):5999-6014.
European Search Report for EP Application 09167115.6 dated Sep. 16, 2009.
Fabian et al,. (1989) "Allele-specific expression of the murine Ren-1 genes," J. Biol. Chem. 264(29):17589-17594.
Fearon (1995) "16 Molecular Abnormalities in Colon and Rectal Cancer," The Molecular Basis of Cancer, pp. 340-357.
Fearon et al. (1990) "A genetic model for colorectal tumorigenesis," Cell. 61(5):759-67.
Feng et al. (2006) "Molecular Biomarkers for Cancer Detection in Blood and Bodily Fluids," Critical Reviews in Clinical Laboratory Sciences, 43(5-6):497-560.
Fournie et al. (1995) "Plasma DNA as a Marker of Cancerous Cell Death. Investigations in Patients Suffering from Lung Cancer and in Nude Mice Bearing Human Tumours," Cancer Letters, 91:221-227.
Frangi et al. (1991) "Nonsense Mutations Affect CI Inhibitor Messenger RNA Levels in Patients with Type I Hereditary Angioneurotic Edema," J. Clinical Invest. 88:755-759.
Fu et al. (1995) "A DNA Sequencing Strategy That Requires Only Five Bases of Known Terminal Sequence for Priming," Proc. NatL Acad Sci. USA, 92: pp. 10162-10166.
Galinsky et al. (1988) "Molecular cloning and sequence analysis of the human parainfluenza 3 virus gene encoding the L protein," Virology, 165(2):499-510.
Gao et al. (1988) "Restriction primer extension method of labeling oligonucleotide probes and its application to the detection of Hb E genes," Hemoglobin, 12(5-6):691-697.
Gardner et al. (2002) "Acyclic and dideoxy terminator preferences denote divergent sugar recognition by archaeon and Taq DNA polymerases," Nucleic Acids Research, 30(2):605-613.
Giacona et al. (1998) "Cell-Free DNA in Human Blood Plasma: Length Measurements in Patients with Pancreatic Cancer and Healthy Controls," Pancreas, vol. 17, No. 1, pp. 89-97.
Gismondi et al. (1997) "Characterization of 19 Novel and Sic Recruoing APC Mutations in Italian Adenomatous Polyposis Patients, Using TWO-Different Mutation Detection Techniques" Human Mutation, vol. 9, No. 4, pp. 370-373.
Godson, (1980) "Primed synthesis methods of sequencing DNA and RNA," Fed. Proc.. 39(10):2822-2829, Abstract only.
Green et al. (1980) "Targeted deletions of sequences from closed circular DNA," Proc. Natl. Acad. Sci. 77(5):2455-2459.
Greene et al. (2001) "A Novel Method for SNP Analysis Using Fluorescence Polarization," Perkin Elmer Life Sciences.
Grossman et al. (1988) "Colonoscopic Screening of persons With Suspected Risk Factors for Colon Cancer" Gastmenterologv 94:395-400.
Gyllensten et al. (1995) "Sequencing of in Vitro Amplified DNA," Recombinant DNA Methodology II, (Wu, ed.) pp. 565-578.
Hasegawa et al. (1995) "Detection of K-ras Mutations in DNAs Isolated From Feces of Patients with Colorectal Tumors by Mutant-Allele-Specific Amplification (MASA)" Oncogene, vol. 10, pp. 1441-1445.
Herman (2002) "Hypermethylation pathways to colorectal cancer. Implications for prevention and detection," Gastroenterol Clin North Am. 31(4):945-58.
Herman JG, et al. (1996) "Methylation-specific PCR: A novel PCR assay for methylation status of CpG islands," Proc Natl Acad Sci USA 93:9821-9826.
Hesson et al. (2003) "NORE1A, a homologue of RASSF1A tumour suppressor gene is inactivated in human cancers," Oncoqene. 22(6):947-54.
Hesson et al. (2004) "Frequent epigenetic inactivation of RASSF1A and BLU genes located within the critical 3p21.3 region in gliomas," Oncogene 23( 3):2408-19.
Hesson et al. (2005) "CpG island promoter hypermethylation of a novel Ras-effector gene RASSF2A is an early event in colon carcinogenesis and correlates inversely with K-ras mutations," Oncogene 24:3987-3994.
Hickman et al. (1994) "Apoptosis and cancer chemotherapy," Phil. Trans R. Soc. Lond., 345:319-325.
Hoang et al. (1997) "BAT-26, an Indicator of the Replication Error Phenotype in Colorectal Cancers and Cell Lines" Cancer Research 57: 300-303.
Hollstein et al. (1991) "p53 Mutations in Human Cancers," Science, vol. 253, pp. 49-53.
Honchel et al. (1995) "Genomic Instability in Neoplasia," Seminars in Cell Biology, vol. 6, pp. 45-52.
Hornes et al. (1990) "Emerging Techniques: Magnetic DNA Hybridization Properties of Oligonucleotide Probes Attached to Superparamagnetic Beads and Their Use in the Isolation of Poly(A) mRNA From Eukaryotic Cells," GATA 7(6):145-150.
Hoss et al. (1992) "Excrement Analysis by PCR" Scientific Correspondence pp. 199.
Hunkapiller et al. (1984) "A microchemical facility for the analysis and synthesis of genes and proteins," Nature 310:305-311.
Iacopetta et al. (1998) "Rapid and Nonisotopic SSCP-based Analysis of the BAT-26 Mononucleotide Repeat for Identification of the Replication Error Phenotype in Human Cancers," Human Mutation 12:355-360.
Iino et al. (1999) "DNA Microsatellite Instability in Hyperplastic Polyps, Serrated Adenomas, and Mixed Polyps: a Mild Mutator Pathway for Colorectal Cancer?" Journal of Clinical Pathology 52: 5-9.
Ikonen et al. (1992) "Quantitative Determination of Rare mRNA Species by PCR and Solid-phase Minisequencing," Cold Spring Harbor Laboratory Press, ISSN 1054-8903, pp. 234-240.
Iniesta et al. (1998) "Genetic Abnormalities and Microsatellite Instability in Colorectal Cancer" Cancer Detection and Prevention 22:383-395.
International Search Report for PCT/US99/08849 (Sep. 13, 1999).
International Search Report for PCT/US03/04827 (Sep. 4, 2003).
International Search Report for PCT/US05/016518, No Date Provided.
International Search Report for PCT/US05/30942, No Date Provided.
International Search Report for PCT/US05/39670 (Apr. 12, 2006).
Irimia et al. (2004) "CpG island promoter hypermethylation of the Ras-effector gene NORE1 A occurs in the context of a wild-type K-ras in lung cancer," Oncogene. 23(53):8695-9.
Ishimaru et al. (1995) "Microsatellite Instability in Primary and Metastatic Colorectal Cancers" International Journal of Cancer 64:153-157.
Iwaya et al. (1998) "Infrequent Fratneshift Mutations of Polynucleotide Repeats in Multiple Primary Cancers Affecting the Esophagus and Other Organs" Genes, Chrom & Cancer 23:317-322.

(56) References Cited

OTHER PUBLICATIONS

Jack et al. (2002) "Kicking the Sugar Habit: AcyNTP Terminator Incorporation by Vent DNA Polymerase" HGH2002 Poster Abstracts: 12. New Technologies, Poster No. 621, Abstract only.
Jarvinen et al. (1995) "Screening Reduces Colorectal Cancer Rate in Families With Hereditary Nonpolyposis Colorectal Cancer" Gastroenterology 108: 1405-1411.
Jeffreys et al. (2003) "DNA enrichment by allele-specific hybridization (DEASH): a novel method for haplotyping and for detecting low-frequency base substitutional variants and recombinant DNA molecules," Genome Research, 13:2316-2324.
Jernvall et al. (1999) "Microsatellite Instability: Impact on Cancer Progression in Proximal and Distal Colorectal Cancers" European Journal of Cancer 35:197-201.
Jessup et al. (1992) "The Biology of Colorectal Carcinoma," Current Problems in Cancer pp. 263-328.
Jonsson et al. (1995) "From Mutation Mapping to Phenotype Cloning," Proc. Natl. Acad. Sci., vol. 92 pp. 83-85.
Kainz et al. (1989) "A modified primer extension procedure for specific detection of DNA-RNA hybrids on nylon membranes," 179(2):366-370, Abstract only.
Kawakami et al. (2000) "Hypermethylated APC DNA in Plasma and Prognosis of Patients with Esophageal Adenocarcinoma," Journal of the National Cancer Institute, 92(22):1805-1811.
Khokhlatchev et al. (2002) "Identification of a novel Ras-regulated proapoptotic pathway," Curr Biol. 12(4):253-65.
Kieleczawa et al. (1992) "DNA Sequencing by Primer Walking with Strings of Contiguous Hexamers," Science,258: pp. 1787-1791.
Kim et al. (2006) "CpG island methylation of genes accumulates during the adenoma progression step of the multistep pathogenesis of colorectal cancer," Genes Chromosomes Cancer 45:781-789.
Kim et al. (1998) Microsatellite Instability in Young Patients With Colorectal Cancee' Pathology International 48: 586-594.
Ko et al. (1999) "Genomic Instability and Alterations in Apc, Mcc and Dcc in Hong Kong Patients with Colorectal Carcinoma," Int. J. Cancer (Pred. Onco1.1, 84:404-409.
Komher at al. (1989) "Mutation detection using nucleotide settings that alter electrophoretic mobility," Nucleic Acids Research, 17(19):7779-7784.
Kondo et al. (2004) "Epigenetic changes in colorectal cancer," Cancer Metastasis Rev. 23(1-2):29-39.
Konishi et al. (1996) "Molecular Nature of Colon Tumors in Hereditary Nonpolyposis Colon Cancer, Familial Polyposis, and Sporadic Colon Cancer" Gastroenterology 1 1 I : 307-317.
Kotler et al, (1993) "DNA Sequencing: Modular Primers Assembled from a Library of Hexamers or Pentamers," Proc. Natl. Acad Sci. USA, 90: pp. 4241-4245 (May 1993).
Krook et al. (1992) "Rapid and simultaneous detection of multiple mutations by pooled and multiplex single nucleotide primer extension: application to the study of insulin-responsive glucose transporter and insulin receptor mutations in non-insulin-dependent diabetes," Human Molecular Genetics, vol. 1, No. 6, pp. 391-395.
Kuppuswamy et al. (1991) "Single Nusleotide primer extension to detect genetic diseases: Experiemental application to hemophilia B (factor IX) and Cystic fibrosis genes," Proc. Natl. Acad. Sci., 88:1143-1147.
Lamberti et al. (1999) "Microsatellite Instability—a Useful Diagnostic Tool to Select Patients at High Risk for Hereditary Non-Polyposis Colorectal Cancer: A Study in Different Groups of Patients With Colorectal Cancer" Gut 44:839-843.
Lebacq (1992) "Polymerase chain reaction and other methods to detect hot-spot and multiple gene mutations," Advances in Clinical Biology, vol. 50, pp. 709-712.
Lee et al, (1992) DNA sequencing with dye-labeled terminators and T7 DNA polymerase: effect of dyes and dNTPs on incorporation of dye-terminators.
Lengauer et al. (1998) "Genetic Instabilities in Human Cancers," Nature, vol. 396, pp. 643-649.

Leong et al. (1993) "Detection of MYCN Gene Amplification and Deletions of Chromosome Ip in Neuroblastoma by in Situ Hybridization Using Routine Histologic Sections," Laboratorv Investigations, vol. 69, No. 1, pp. 43-50.
Lerman et al. (2000) "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium," Cancer Res. 60(21):6116-33.
Lin et al. (1998) "Colorectal and Extracolonic Cancer Variations in MLHI/MSH2 Hereditary Nonpolyposis Colorectal Cancer Kindreds and the General Population" Diseases of the Colon & Rectum 41:428-433.
Lipkin et al. (1998) "Quantitative Trait Locus Mapping in Dairy Cattle by Means of Selective Milk DNA Pooling Using Dinucleotide Microsatellite Markers: Analysis of Milk Protein Percentage" Genetics 49:1557-1567.
Litia et al. (1992) "Simultaneous Detection of TWO-Cystic Fibrosis Alleles Using Dual-Label Time-Resolved Fluorometry," Molecular and Cellular Probes, vol. 6, pp. 505-512.
Liu et al. (2003) "Control of microtubule stability by the RASSF1 A tumor suppressor," Oncogene. 22(50):8125-36.
Liu et al. (1986) "Synthesis of a fixed-length single -stranded DNA probe by blocking primer extension in bacteriophage M13," Gene, 42:113-117.
Lleonart et al. (1998) "Microsatellite Instability and p53 Mutations in Sporadic Right and Left Colon Carcinoma" American Cancer Society 83:889-895.
Lo et al. (1984) "Specific amino acid substitutions in bacterioopsin: Replacement of a restriction fragments containing altered codons," Proc. Natl. Acad. Sci., 81:2285-2289.
Loktionov A. and I. K. O'Neill, (1995) "Early Detection of Cancer-Associated Gene Alterations in DNA Isolated from Rat Feces During Intestinal Tumor Induction with 1,2-Dimethylhydrazine," International Journal of Oncology, vol. 6, pp. 437-445.
Loktionov et al. (1998) "Quantitation of DNA from Exfoliated Colonocytes Isolated from Human Stool Surface as a Novel Non-invasive Screening Test for Colorectal Cancer," Clinical Cancer Research, vol. 4, pp. 337-341.
Lathe, et al. (1998) "The APC Gene 11307K Variant is Rare in Norwegian Patients with Familial and Sporadic Colorectal or Breast Cancer" Cancer Research, vol. 58, pp. 2923-2924.
Luo et al. (1988) "Point mutations in glycoprotein gene of vesicular stomatitis virus (New Jersey serotype) selected by resistance to neutralization by epitope-specific monoclonal antibodies," Virology, 163(2):341-348.
Makristathis et al. (1998) "Detection of Helicobacter pylori in Stool Specimens by PCR and Antigen Enzyme Immunoassay," Journal of Clinical Microbiology, vol. 36, No. 9, pp. 2772-2774.
Mao L. et al. (1996) "Molecular Detection of Primary Bladder Cancer by Microsatellite Analysis," Science. vol. 271, pp. 659-662.
Matteucci et al. (1981) "Studies on Nucleotide Chemistry IV. Synthesis of Deoxyoligonucleotides on a Polymer Support," J. Am. Chem. Soc., 103:3185-3191.
Maxam et al. (1977) "A new method for sequencing DNA," Proc. Natl. Acad. Sci., 74(2):560-564, Abstract only.
Medeiros et al. (1989) "M13 Bioprints: non-isotopic detection of individual-specific human DNA fingerprints with biotinylated M13 bacteriophage," Forensic Sci. Int., 43(3):275-280.
Meijers-Heijboer et al. (1999) "Familial Endometrial Cancer in Female Carriers of MSH6 Germline Mutations" Nature Genetics 23: 142-144.
Middendorf et al. "8 Sequencing Technology," pp. 183-198, No Date Provided.
Miller et al. (1997) "Semiautomated Resolution of Overlapping Stutter Patterns in Genomic Microsatellite Analysis" Analytical Biochemistry 251:50-56.
Mills, Stacey E. (2001) "Digital Diagnoses in an Analog World," American Society for Clinical Pathology Editorial, two pages.
Morinaga et al. (1984) "Improvement of Oligonucleotide—Directed Site-Specific Mutagenesis Using Double-Stranded Plasmid DNA," Biotechnology pp. 636-639.

(56) References Cited

OTHER PUBLICATIONS

Muller et al. (2004) "Methylation changes in faecal DNA: a marker for colorectal cancer screening?" Lancet. 363(9417):1283-5.
Myers, R.M. (1993) "The Pluses of Subtraction," Science. vol. 259, pp. 942-943.
Naber (1994) "Molecular Pathology—Detection of Neoplasia," New England Journal of Medicine, vol. 331, No. 22, pp. 1508-1510.
Netzer, P. et al. (1997) "Screening sigmoidoscopy or colosopy for detection of colorectal adenomas and cancers?" Gastroenterology, 112(4):A626, Abstract only.
Nikiforov et al. (1994) "Genetic Bit Analysis: a solid phase method for typing single nucleotide polymorphisms," Nucleic Acids Research, vol. 22, No. 20, pp. 4167-4175, Abstract only.
Nollau et al. (1996) "Detection of K-ras Mutations in Stools of Patients with Colorectal Cancer by Mutant- Enriched PCR," Int. J. Cancer, vol. 66 pp. 332-336.
Nollau et al. (1996) "Isolation of DNA from Stool and Bodily Fluids for PCR Amplication," BioTechniques, vol. 20, No. 5, pp. 784-788.
Olsen et al. (1989) "Incomplete primer extension during in vitro DNA amplification catalyzed by Taq polymerase; exploitation for DNA sequencing," Nucleic Acids Res.. 17(23):9613-9620, Abstract only.
Olson et al. (2005) "DNA stabilization is critical for maximizing performance of fecal DNA based colorectal cancer tests," Diaqn Mol Pathol 14:183-191.
Orlow et al. (1995) "Deletion of the p16 and p15 Genes in Human Bladder Tumors Journal of the National Cancer Institute" vol. 87, No. 20, pp. 1524-1529.
Ortiz-Vega et al. (2002) "The putative tumor suppressor RASSF1 A homodimerizes and heterodimerizes with the Ras-GTP binding protein Nore1," Oncogene. 21(9):1381-90. Erratum in: Oncogene 21(12):1943.
Palmieri et al. (1999) "Polymerase Chain Reaction-Based Detection of Circulating Melanoma Cells as an Effective Marker of Tumor Progression," Journal of Clinical Oncology, 17(1): 304-311.
Park et al.(1999) "Gene-Environment Interaction in Hereditary Nonpolyposis Colorectal Cancer with Implications for Diagnosis and Genetic Testing" International Journal of Cancer 82: 516-519.
Parker et al. (1988) "Interaction of 2-Halogenated dATP analogs (F, Cl and Br) with human DNA polymerases, DNA primase, and ribonucleotide reductase," Mol. Pharmacol., 34(4):485491, Abstract only.
Peattie, (1979) "Direct chemical method for sequencing RNA," Proc. Natl. Acad. Sci., 76(4):1760-1764.
Peltomaki et al (1997) "Mutations Predisposing to Hereditary Nonpolyposis Colorectal Cancer: Database and Results of a Collaborative Study" Gastroenterology 113: 1146-1158.
Perlin et al. (1995) "Toward Fully Automated Tenotyping: Genotyping Microsatellite Markers by Deconvolution" American Journal of Human Genetics 57:1199-1210.
Pharmacia (1991/1992) Molecular and Cell Biology Catalogue, pp. 8.3-8.6.
Pharmacia (1998) BioDirectorv, pp. 104-109.
Piao et al. (1997) "Relationship between Loss of Heterozygosity of Tumor Suppressor Genes and Histologic Differentiation in Hepatocellular Carcinoma," Cancer, vol. 80, No. 5, pp. 865-872.
Ponz de Leon et al. (1998) "Frequency and Type of Colorectal Tumors in Asymptomatic High Risk Individuals in Families with Hereditary Nonpolyposis Colorectal Cancer" Cancer Epidemiology, Biomarkers & Prevention 7: 639-641.
Ponz de Leon et al. (1999) "Hereditary Colorectal Cancer in the General Population: From Cancer Registration to Molecular Diagnosis" Gut 45: 32-38.
Praskova et al. (2004) "Regulation of the MST1 kinase by autophosphorylation, by the growth inhibitory proteins, RASSF1 and NORE1, and by Ras," Biochem J. 381(Pt 2):453-62.
Prober et al. (1987) "A System for Rapid DNA Sequencing with Fluorescent Chain-Terminating Dideoxynucleotides," Research Articles, pp. 336-341.

Pyatt et al. (1999) "Polymorphic Variation at the BAT-25 and BAT-26 Loci in Individuals of African Origin" American Journal of Pathology 155: 349-353.
Raff (1998) "Cell Suicide for Beginners," Nature, vol. 396, pp. 119-122.
Rashid et al. (1999) "Genetic Epidemiology of Mutated K-ras Proto-Oncogene, Altered Suppressor Genes, and Microsatellite Instability in Colorectal Adenomas" Gut 44: 826-833.
Ravelingien et al. (1995) "Contribution of Molecular Oncology in the Detection of Colorectal Carcinomas," Acta Gastro-Enterologica Belgic a, vol. 58, pp. 270-273.
Rhyu (1996) Molecular Mechanisms Underlying Hereditary Nonpolyposis Colorectal Carcinoma, Journal of the National Cancer Institute, vol. 88, No. 5, pp. 240-251.
Rice et al. (2001) "Identification of single nucleotide polymorphisms (SNPs) and other sequence changes and estimation of nucleotide diversity in coding and flanking regions of the NMDAR1 receptor gene in schizophrenic patients," Molecular Psychiatry, 6(3):274-284.
Ridanpaa et al. (1995) Detection of Loss of Heterozygosity in the p53 Tumor Suppressor Gene Using a PCR-based Assay, Path. Res. Pract., vol. 191, pp. 399-402.
Riegler et al. (1999) "Prevalence of HNPCC in a Series of Consecutive Patients on the First Endoscopic Diagnosis of Colorectal Cancer: A Multicenter Study" Endoscopy 31: 337-341.
Rinaldy et al. (1988) "Gene Cloning Using cDNA Libraries in a Differential Competition Hybridization Strategy: Application to Cloning XP-A Related Genes," DNA 7(8):563-70.
Rodriguez-Bigas et al. (1997) "A National Cancer Institute Workshop on Hereditary NonpolyposisColorectal Cancer Syndrome: Meeting Highlights and Bethesda Guidelines" Journal of the National Cancer Institute 89:1758-1762.
Roemer et al (2000) "Sequencing BAC DNA With Near-Infrared Flourescent Non-Nucleotide Terminators," LI-COR On-line Poster 530, LI-COR, Inc., Biotechnology, Lincoln, Nebraska, nine pages.
Rosenthal et al. (1985) "Solid-phase methods for sequencing of nucleic acids, I. Simultaneous sequencing different oligodeoxyribonucleotides using a new, mechanically stable anion-exchange paper," Nucleic Acids Research, 13(4):1173-1184.
Runnebaum et a. (1994) "Multiplex PCR Screening detects small p53 deletions and insertions in human ovarian cancer cell lines," Human Genetics, vol. 93, pp. 620-624.
Salahshor et al. (1999) "Microsatellite Instability in Sporadic Colorectal Cancer is Not an Independent Prognostic Facto(" British Journal of Cancer 81: 190-193.
Sambrook et al. (1989) "Molecular Cloning," Second Edition, p. 13.67-13.69.
Samiotaki et al. (1994) "Dual-Color Detection of DNA Sequence Variants by Ligase-Mediated Analysis," Genomics 20:238-42.
Samowitz et al. (1995) "Microsatellite Instability in Human Colonic Cancer Is Not a Useful Clinical Indicator of Familial Colorectal Cancer" Gastroenterology 109: 1765-1771.
Samowitz et al. (1997) "Microsatellite Instability in Colorectal Adenomas" Gastroenterology 112: 1515-1519.
Samowitz et al. (1999) "BAT-26 and BAT-40 Instability in Colorectal Adenomas and Carcinomas and Germline Polymorphisms" American Journal of Pathology 154:1637-1641.
Samuels et al. (2004) "High frequency of mutations of the PIK3CA gene in human cancers," Science, 304(5670):554.
Sanger et al. (1975) "A Rapid Method for Determing Sequences in DNA by Primed Synthesis with DNA Polymerase" J. Mol. Biol.. 94:441-448.
Sanger et al. (1977) "DNA Sequencing with Chain-Terminating Inhibitors" Proc. Natl. Acad. Sci. USA, vol. 74, No. 12, pp. 5463-5467.
Segel (1976) "Double Label Analysis," Biochemical Calculations, 2d ed., pp. 373-376.
Sheehan et al. (1987) "Reducing agent-sensitive dimerization of the hemagglutinin-neuraminidase glycoprotein of Newcastle disease virus correlates with the presence of cycteine at residue 123," Virology, 161(2):603-606.

(56) References Cited

OTHER PUBLICATIONS

Shitoh et al. (1998) "Important Microsatellite Markers in the Investigation of RER in Colorectal Cancers," Jim. J. Cli, Oncol vol. 28, No. 8, pp. 538-541.
Shivakumar et al. (2002) "The RASSF1A tumor suppressor blocks cell cycle progression and inhibits cyclin D1 accumulation," Mol Cell BioL 22(12):4309-18.
Shortle et al, (1980) "Segment-directed mutagenesis: Construction in vitro of point mutations limited to a small predetermined region of a circular DNA molecule," Proc. Natl. Acad. Sci., 77(9):5375-5379.
Shortle et al. (1981) "Directed Mutagenesis," Ann. Rev. Genet. 15:265-294.
Shortle et al. (1982) "Gap misrepair mutagenesis: Efficient site-directed induction of transition, transversion, and frameshift mutations in vitro," Proc. Natl. Acad. Sci., 79:1588-1592.
Shumaker et al. (1996) "Mutation Detection by Solid Phase Primer Extension," Human Mutation, vol. 7, pp. 346-354.
Sidransky et al. (1992) "Identification of ras Oncogene Mutations in the Stool of Patients with Curable Colorectal Tumors," Science, vol. 256, pp. 102-105.
Singer et al. (1989) "Effect of 3' flanking neighbors on kinetics of pairing of dCTP or dTTP opposite O6-methylguanine in a defined primed oligonucleotide when *Escherichia coli* DNA polymerase I is used," Proc. Natl. Acad. Sci., 86:8271-8274.
Singer-sam et al. (1992) "A Sensitive, Quantitative Assay for Measurement of Allele-specific Transcripts Differing by a Single Nucleotide," PCR Methods and Applications. 1:160-163.
Smith-Ravin et al. (1995) "Detection of c-Ki-ras Mutations in Fecal Samples from Sporadic Colorectal Cancer Patients," Gut, vol. 36, pp. 81-86.
Sokolov, (1989) "Primer extension technique for the detection of single nucleotide in genomic DNA,"Nucleic Acids Research, 18(12):3671.
Srinivas et al. (2001) "Trends in biomarker research for cancer detection," The Lancet, 2: 698-704.
Stahl et al. (1988) "Solid phase DNA sequencing using the biotin-avidin system," Nucleic Acids Research, 16(7):3025-3038.
Suzuki et al. (2002) "A genomic screen for genes upregulated by demethylation and histone deacetylase inhibition in human colorectal cancer," Nat Genet 31(2):141-9. Epub May 6, 2002.
Syngal et al. (1998) "Benefits of Colonoscopic Surveillance and Prophylactic Colectomy in Patients With Hereditary Nonpolyposis Colorectal Cancer Mutations," Annals of Internal Medicine 129: 787-796.
Syngal et al. (1999) "Interpretation of Genetic Test Results for Hereditary Nonpolyposis Colorectal Cancer" JAMA 282: 247.
Syvanen (1994) Detection of Point Mutations in Human Genes by the Solid-phase Minisequencing Method, Clinica Chimica Acta, vol. 226, pp. 225-236.
Syvanen et al. (1990) "A primer-Guided Nucleotide Incorporation Assay in the Genotyping of Apolipoprotein E," Genomics, 8:684-692.
Syvänen, (1997) "Solid-Phase Minisequencing," Detection of Mutations and Polymorphisms in DNA, Chapter 6, pp. 53-64.
Tagore et al. (2003) "Sensitivity and Specificity of a Stool DNA Multitarget Assay Panel for the Detection of Advanced Neoplasia," Clinical Colorectal Cancer, 3(1):47-53.
Takeda et al. (1993) "Detection of K-ras Mutation in Sputum by Mutant-Allele-Specific Amplification (MASA)" Human Mutation, vol. 2, pp. 112-117.
Thibodeau et al. (1993) "Microsatellite Instability in Cancer of the Proximal Colon," Science, vol. 260, pp. 816-819.
Thiede et al. (1996) "Simple and sensitive detection of mutations in the ras proto-oncogene using PNA-mediated PCR clamping," Nucleic acids research, 24:983-984.
Tommasi et al. (2002) "RASSF3 and NORE1: identification and cloning of tWO-human homologues of the putative tumor suppressor gene RASSF1" Oncogene. 21(17):2713-20.
Toyota et al. (1999) "CpG island methylator phenotype in colorectal cancer," Proc Nat. Acad Sci USA 96:8681-8686.
Traverso et al. (2002) "Detection of APC Mutations in Fecal DNA from Patients with Colorectal Cancer," N. Engl. J. Med.. 346(5):311-320.
Ugozzoli, et al. (1992) "Detection of Specific Alleles by Using Allele-Specific Primer Extension Followed by Capture on Solid Support," CATA 9(4): pp. 107-112.
Van Engeland et al. (2002) "K-ras mutations and RASSF1 A promoter methylation in colorectal cancer," Oncogene. 21(23):3792-5.
Vasen et al. (1993) "Surveillance in Hereditary Nonpolyposis Colorectal Cancer: An International Cooperative Study of 165 Families" Diseases of the Colon & Rectum) 36:1-4.
Vasen et al. (1998) "A Cost-Effectiveness Analysis of Colorectal Screening of Hereditary Nonpolyposis Colorectal Carcinoma Gene Carriers" American Cancer Society 82:1632-1637.
Vasen et al. (1999) "New Clinical Criteria for Hereditary Nonpolyposis Colorectal Cancer (HNPCC, Lynch Syndrome) Proposed by the International Collaborative Group on HNPCC" Gastroenterology, 116:1453-1456.
Vavvas et al. (1998) "Identification of Nore1 as a potential Ras effector," J Biol Chem. 273(10):5439-42.
Villa et al. (1996) "Identification of Subjects at Risk for Colorectal Carcinoma Through a Test Based on K-ras Determination in the Stool," Gastroenterology, vol. 110, No. 5, pp. 1346-1353.
Vogelstein, B. and Kinzler, K.W., (1999) "Digital PCR," Proc. NatL Acad. Sci. USA, vol. 96, pp. 9236-9241.
Vos et al. (2003) "RASSF2 is a novel K-Ras-specific effector and potential tumor suppressor," J Biol Chem. 278(30):28045-51.
Vos et al. (2004) "A role for the RASSF1 A tumor suppressor in the regulation of tubulin polymerization and genomic stability," Cancer Res. 64(12).4244-50.
Vreeland et al. (2002) "Multiplexed, High-Throughput Genotyping by Single-Base Extension and End- Labeled Free-Solution Electrophoresis," Anal. Chem. 74:4328-4333.
Wada et al. (1983) "Automatic DNA sequencer: Computer-programmed microchemical manipulator for the Maxam-Gilbert sequencing method," Rev_Sci. Instrum., 54(11):1569-1572.
Wagner et al. (2002) "Frequent RASSF1A tumour suppressor gene promoter methylation in Wilms' tumour and colorectal cancer," Oncoqene. 21 (47):7277-82.
Wallace et al. (1979) "Hybridization of Synthetic Oligodeoxyribonucleotides to <DT 174 DNA: the Effect of Single Base Pair Mismatch," Nucleic Acids Research, vol. 6, No. 11, pp. 3543-3557.
Walsh et al. (1996) "Sequence Analysis and Characterization of Stutter Products at the Tetranucleotide Repeat Locus vWA," Nucleic Acids Research vol. 24, No. 14, 2807-2812.
Walsh et al. (1992) "Preferential PCR Amplification of Alleles: Mechanisms and Solutions," PCR Methods and Applications, pp. 241-250.
Wang et al. (1998) Large-Scale Identification, Mapping, and Genotyping of Single Nucleotide Olymorphisms in the Human Genome, Science, vol. 280, pp. 1077-1082.
Watson et al. (1994) "Isolation of Differentiality Expressed Sequence Tags from Human Breast Cancer," Advances in Brief XP 000576043 pp. 4598-4602.
Whitney et al. (2004) "Enhanced retrieval of DNA from human fecal samples results in improved performance of colorectal cancer screening test," J Mol Diagn. 6:386-395.
Written opinion for PCT/US05/30942, No Date Provided.
Written opinion for PCT/US05/39670 dated Apr. 12, 2006.
Young G.P., and B.H. Demediu, (1992) "The Genetics, Epidemiology, and Early Detection of Gastrointestinal Cancers" Current Opinion in Oncology, vol. 4, pp. 728-735.
Zakour et al. (1984) "Site specific mutagenesis: insertion of single noncomplementary nucleotides at specified sites by error-directed DNA polymerization," Nucleic Acids Research, 12(16):6615-6628.
Zhang et al. (2006) "Inactivation of RASSF2A by promoter methylation correlates with lymph node metastasis in nasopharyngeal carcinoma," International Journal of Cancer, 120:32-38.

(56) References Cited

OTHER PUBLICATIONS

Zhou et al. (1997) "Allelic Profiles of Mononucleotide Repeat Microsatellites in Control Individuals and in Colorectal Tumors With and Without Replication Errors" Oncoeene 15: 1713-1718.

Zhou et al. (1998) "Determination of the Replication Error Phenotype in Human Tumors Without the Requirement for Matching Normal DNA by Analysis of Mononucleotide Repeat Microsatellites" Genes. Chromosomes & Cancer 21: 101-107.

Zimmern et al. (1978) "3'-Terminal nucleotide sequence of encephalomyocarditis virus RNA determined by reverse transcriptase and chain-terminating inhibitors," Proc. Natl. Acad. Sci., 75:4257-4260.

Zitt et al. (2007) "DNA methylation in colorectal cancer," Disease Markers 23(1-2):51-71.

Zoller et al. (1982) "Oligonucleotide-directed mutagenesis using M13-derived vectors: an efficient and general procedure for the production of point mutations in any fragment of DNA," Nucleic Acids Research, 10(20):6487-6500.

Moore et al., An electrophoretic capture method for efficient recovery of rare sequences from heterogeneous DNA, BioTechniques, 2008, 44:363-374.

Piepenburg, O. et al., DNA Detection using Recombination Proteins, PLoS Biol., 2006, 4(7): e204, pp. 1115-1121.

\* cited by examiner

ANALYSIS OF HETEROGENEOUS NUCLEIC ACID SAMPLES

CROSS-REFERENCE TO RELATED APPLICATIONS

This application is the national stage of International (PCT) Patent Application Serial No. PCT/US2006/015062, filed Apr. 21, 2006, and published under PCT Article 21(2) in English, which claims priority to and the benefit under 35 U.S.C. §119(e) of U.S. provisional application Ser. No. 60/673,436, filed Apr. 21, 2005 and U.S. provisional application Ser. No. 60/728,996, filed Oct. 20, 2005, the entire contents of both are herein incorporated by reference.

FIELD OF THE INVENTION

The invention relates to methods for detecting genetic alterations in biological samples.

BACKGROUND OF THE INVENTION

Different sequencing methods have been used to detect mutations in biological samples. However, improved methods for detecting mutations at the early stages of diseases are needed.

SUMMARY OF THE INVENTION

Aspects of the invention relate to methods for detecting indicia of diseases (e.g., adenoma, precancer, cancer, etc.) in biological samples, particularly heterogeneous biological samples (e.g., stool samples) that may contain high amounts of normal nucleic acid relative to mutant nucleic acid indicative of disease. In one aspect, methods of the invention involve combining a low genome complexity preparative step (e.g., a preparative step that yields a sample with low genome complexity) with a high genome complexity analytical step (e.g., a step that can analyze and/or sequence a sample of high genome complexity) in order both to isolate and detect rare nucleic acid molecules indicative of the presence of a disease in a subject from which a biological sample was obtained. The subject may be a human or other mammal. The subject may be a patient with known risk factors or symptoms for disease. The subject may be an individual that is being screened for indicia of disease. Accordingly, aspects of the invention are useful in a population screen to identify subjects with indicia of a disease associated with the presence of abnormal (e.g., mutant) nucleic acid in a biological sample that also contains normal nucleic acid.

According to the invention, the presence of disease (e.g., an adenoma and/or early stage cancer) may be indicated by the presence, in a heterogeneous biological sample, of an altered/mutant nucleic acid molecule at a very low frequency relative to the corresponding normal nucleic acid molecule (for example, about 1% or lower, e.g., lower than about 0.1%, 0.01%, 0.001%, 0.0001%, or even lower). According to aspects of the invention, an altered/mutant nucleic acid molecule originating from disease (e.g., an adenoma and/or early stage cancer) cell (or debris thereof) may be shed into a biological sample along with a large number of corresponding normal nucleic molecules that are shed from normal cells (i.e., non-adenoma and non-cancer cells) that line a lumen from which the biological sample originates or is obtained. For example, an adenoma or early stage cancer is typically small and very few diseased cells (or debris thereof) are shed into the biological sample relative to normal cells (or debris thereof) from the normal tissue surrounding the adenoma or early stage cancer. As a result, altered/mutant nucleic acid molecules indicative of the adenoma or early stage cancer may be very rare relative to the corresponding normal nucleic acid molecules (i.e., nucleic acid molecules with an unaltered or non-mutant sequence from the same region of the genome as the altered/mutant nucleic acid molecule that has the altered/mutant sequence).

In order to detect rare nucleic acid molecules indicative of adenoma or early stage cancer, aspects of the invention involve using a high yield capture step in order to isolate a statistically sufficient number of target nucleic acid molecules (nucleic acid molecules that contain the sequence suspected of being altered/mutant) from a biological sample. A statistically sufficient number of target nucleic acid molecules is a number that is sufficiently large for an altered/mutant nucleic acid molecule (if present) to be captured with statistical significance (e.g., with greater than about 90%, greater than about 95%, or greater than about 99% probability). However, a rare altered/mutant nucleic acid molecule is typically captured along with a vast excess of normal nucleic acid molecules. According to the invention, the rare nucleic acid molecule (if present in the captured preparation of nucleic acid molecules) may be detected by interrogating the captured preparation using an analytical technique that is designed for analyzing or sequencing nucleic acid samples with high genome complexity even though most (or all) of the captured nucleic acid molecules have identical or substantially identical (e.g., overlapping) sequences. According to the invention, an analytical technique designed for analyzing or sequencing nucleic acid samples with high genome complexity may be used to detect rare nucleic acid molecules having a sequence that differs from the sequence of a vast excess of normal nucleic acid molecules that are present in a preparation of nucleic acid molecules captured (e.g., using a high yield capture technique) from a biological sample.

Accordingly, in one aspect, the invention involves sequence specific nucleic acid hybrid capture and single molecule nucleic acid sequencing or characterization. In one aspect, the invention involves sequence specific nucleic acid hybrid capture and digital nucleic acid sequencing or characterization. In one embodiment, the hybrid capture enriches a sample for a low complexity target nucleic acid molecule suspected of containing a mutation or alteration indicative of adenoma or early stage cancer (e.g., in a human). A statistically significant analysis may be performed when a statistically significant number of genome equivalents of the target molecule are captured. A genome equivalent of a target molecule is the number of copies of that target molecule that are present in a genome (e.g., a single copy gene or genetic locus may be present in 2 copies in a single genome in the form of 2 alleles, for example a 7 pg DNA sample may represent a single genome and contain 2 copies of a single copy gene or genetic locus). Accordingly, isolating a predetermined number of genome equivalents of a target molecule comprises isolating the predetermined number of copies of the target molecule. Other genomic nucleic acid sequences do not need to be isolated in order to obtain the predetermined number of genome equivalents of the target molecule. Nonetheless, it should be appreciated that additional nucleic acids may be isolated or captured along with the target nucleic acid. However, in certain embodiments, the sequence analysis of the target molecules is more efficient and/or easier and/or more accurate when fewer additional nucleic acid molecules other than the target molecule are isolated.

DETAILED DESCRIPTION OF THE INVENTION

Figure 1:
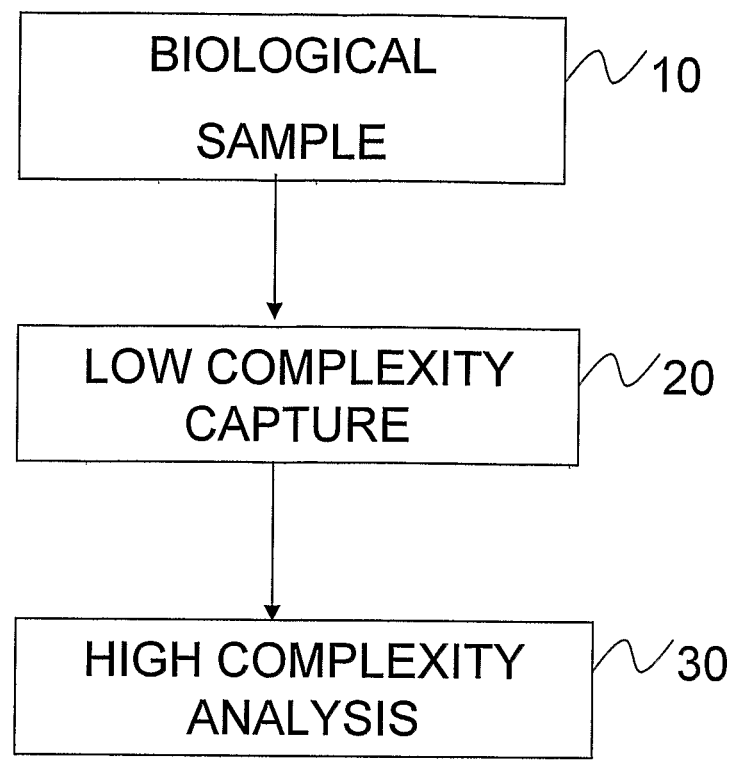
FIG. 1 is a flow diagram of an analysis method.

Aspects of the invention relate to detecting one or more rare nucleic acids in heterogeneous biological samples. FIG. 1 illustrates one embodiment of the invention where a low complexity capture technique is combined with a high complexity analytical technique to assay for the presence of a rare molecule in a biological sample. In act 10, a biological sample (e.g., a stool sample or other suitable biological sample) is obtained and optionally processed (e.g., to stabilize nucleic acids, to remove particulate matter, to precipitate nucleic acids, to shear nucleic acids, to digest nucleic acids, to label nucleic acids, to modify nucleic acids, etc., or any combination thereof). In act 20, a low complexity capture technique (e.g., using an immobilized capture probe that is complementary to a target nucleic acid) may be used to capture one or more copies of a nucleic acid from a target region of interest. In some embodiments, two or more different immobilized capture probes may be used to capture two or more different nucleic acids of interest (e.g., nucleic acids from two or more different genomic regions of interest). In act 30, a high complexity analytical technique (e.g., a digital analysis, a single molecule sequencing technique, a technique developed for whole genome sequencing, etc., or any combination thereof) may be used to analyze the captured low complexity nucleic acid sample and determine whether one or more rare nucleic acids (e.g., nucleic acids indicative of disease) are present.

Accordingly, aspects of the invention relate to combining single molecule sequence analysis technology (e.g., sequencing technology that was developed for whole genome sequence analysis) with specific sequence capture technology in order to detect rare genetic abnormalities at one or more genetic loci. Accordingly, aspects of the invention allow isolation and detection of very low frequency nucleic acid molecules having rare genetic abnormalities by combining i) a high efficiency specific sequence capture step that yields a nucleic acid preparation of relatively low genomic complexity containing several genome equivalents of a target nucleic acid of interest with ii) a high complexity analytical step, such as single molecule sequence analysis that can be used to characterize (e.g., sequence) each of a plurality of genome equivalents of the target nucleic acid. According to the invention, a high complexity analytical step may be used to detect (for example, with statistically significant confidence, e.g., greater than 90%, greater than 95%, or greater than 99% confidence) the presence or absence of a rare nucleic acid in a preparation of captured nucleic acid molecules having identical or substantially identical sequences.

Aspects of the invention relate to methods for detecting indicia of diseases (e.g., adenomas and/or early stage cancers) in biological samples. In particular, aspects of the invention relate to methods for detecting the presence of rare altered/mutant nucleic acid molecules that are present at a very low frequency in a biological sample containing a majority of normal nucleic acid molecules. According to the invention, altered/mutant nucleic acid indicative of adenoma and/or early stage cancer and/or other diseases may be present only at a frequency of less than 1% (e.g., less that 0.1%) of the total genome equivalents in a biological sample. Aspects of the invention are useful for both isolating and detecting such rare nucleic acid molecules. According to the invention, a detection assay may fail to detect nucleic acid molecules that are present at a very low frequency in a biological sample if either i) a capture step fails to capture a rare nucleic acid molecule that is present in a biological sample and/or ii) a detection reaction fails to detect a rare nucleic acid that is present in a preparation of captured nucleic acid.

According to aspects of the invention, the captured nucleic acid molecules may be relatively small, for example, from about 50 bases long to about several kilo-bases long (e.g., between about 100 bases and 10,000 bases, or about 150 bases, about 200 bases, about 250 bases, about 300 bases, about 350 bases, about 400 bases, about 450 bases, about 500 bases, about 1,000 bases, about 1,500 bases, about 2,000 bases, about 2,500 bases, about 3,000 bases, about 5,000 bases long, etc.). However, longer or shorter nucleic acid molecules may be captured. A typical biological sample may contain (or be processed to contain) nucleic acid fragments distributed across a range of sizes such as those described above. It should be noted that genomic nucleic acid in certain biological samples (e.g., stool samples) is already fragmented with typical fragment sizes ranging from 50 bases to several hundred bases long. A captured nucleic acid may be single stranded, double stranded, or contain both single and double-stranded regions. A captured nucleic acid may be DNA, RNA, or a modified form thereof.

It should be appreciated that aspects of the invention described herein, although particularly useful for the detection of adenomas or early stage cancer, also may detect later stage cancers. An assay with sufficient sensitivity to detect adenomas or early stage cancer will be sufficiently sensitive to detect altered/mutant nucleic acid from a later stage cancer that is present at a higher frequency in a heterogeneous biological sample. Similarly, aspects of the invention may be used to detect other diseases that are associated with the presence of abnormal nucleic acid in a biological sample. Similarly, aspects of the invention may be used to detect the presence, in a biological sample, of nucleic acid abnormalities associated with other diseases. Other diseases may include one or more inflammatory conditions, infections (including, for example, intracellular viral modifications), etc.

It should be appreciated that in order to determine with statistical significance whether an abnormal nucleic acid is present or absent in a biological sample, a minimum or threshold number of genome equivalents of a target nucleic acid need to be characterized (e.g., sequenced in whole or in part) to determine if any one (e.g., two, or more than one or two) of them is abnormal. For suspected rarer abnormalities, higher numbers of genome equivalents may be characterized to reach a statistically significant conclusion that the sample does or does not contain the abnormality. For example, if a mutation is suspected to be present in 1% (if at all) of the copies of a target nucleic acid in a sample, then 100 or more copies (genome equivalents) of the region suspected to be mutant should be characterized. In this embodiment, the result has higher statistical significance if about 200; 300; 400; 500; 600; 700; 800; 900; 1,000 or more (e.g. 1,500; 2,000; 2,500; 5,000; 10,000 genome equivalents) target nucleic acid molecules are sequenced. In one aspect, a statistically significant result may be obtained for an abnormality suspected to be present in x % of the target nucleic acids in a biological sample (or in x % of the captured nucleic acid molecules) if 100/x or more genome equivalents of a target nucleic acid containing the region suspected of being abnormal are characterized. In certain embodiments, about 200/x; about 300/x; about 400/x; about 500/x; about 600/x; about 700/x; about 800/x; about 900/x; about 1,000/x; about 5,000/x; about 10,000/x; about 50,000/x or more genome equivalents are characterized. For example, if a 0.1% level of abnormality is suspected, 1,000 or more genome equivalents should be characterized. Similarly, for a 0.01% level, 10,000 or more genome equivalents should be characterized. Accordingly, appropriate sample volumes and isolation steps should be used to provide sufficient genome equivalents for subsequent analysis. It should be appreciated that less than 100/x genome equivalents may be used under certain circumstances where statistical significance is less important.

In certain embodiments, two or more markers may be analyzed in a single assay. Accordingly, two or more different target nucleic acid regions may be isolated. In one embodiment, the number of genome equivalents of each target molecule is above a threshold number sufficient for a statistically significant result to be obtained upon subsequent sequence analysis of the captured molecules or a portion thereof. In general, the threshold level would be set at the same level for each different abnormality being assayed for in a biological sample.

It should be appreciated that the level of sensitivity (e.g., how low a percentage of abnormality can be detected) may determine the earliest stage at which the presence or absence of a disease may be detected with statistical significance. For example, if a predetermined threshold level of at least 10,000 genome equivalents are characterized, a 0.01% level of mutation may be detected with statistical significance. Detecting a mutation at a 0.01% level allows a disease to be detected earlier than using a 0.1%, 1%, 10% detection level, because the 0.01% level corresponds to a stage in the disease when the diseased cells have not multiplied to a level that would allow them to be detected using a 0.1%, 1%, or 10% detection threshold. Similarly, a 0.1% threshold allows earlier detection than a 1% threshold (and 1% earlier than 10% etc.). Characterizing hundreds or thousands of (e.g., 5,000; 10,000; 50,000; 100,000 or more) copies of a single genetic region or of each of several genetic regions may seem like a large amount of work. However, high complexity analytical methods such as those developed for genome sequencing (and particularly those developed for single molecule sequencing) can be used for this task since they are capable of sequencing many more molecules than required for statistical significance according to the invention. For example, the number of single molecules required for sequencing an entire genome, or even a significant portion of a genome, is greater than the number of single molecules that may be sequenced for statistical significance according to certain aspects of the invention. A particular feature of methods of the invention is that the single molecules being sequenced have similar, identical, or overlapping sequences, because they were isolated as multiple genome equivalents including a locus of interest. This differs from genome sequencing where most of the single molecules being sequenced have different sequences since they are generated to represent different portions of the genome. Accordingly, while methods of the invention use high-complexity analytical techniques, these techniques may be adapted for the particular configurations required by aspects of the invention. For example, a predetermined genetic locus may be analyzed using a single sequencing primer that is expected to work on all of the isolated target molecules. This primer may be sequence specific and contain at least about 10, 15, 20, 25, 30, 35, 40, 45, 50, or more nucleotides that are complementary to a region of the target molecule in proximity with the region suspected of containing an abnormality. In some embodiments, two or more different primers (e.g., 3, 4, 5, 6, 7, 8, 9, 10, etc.) different sequencing primers may be used in different sequencing reactions (for example, each using a threshold number of genome equivalents of target nucleic acid) to provide further confidence in the sequencing results. In contrast, certain genome sequencing methods involve a plurality different primers in a single analysis so that each primer can hybridize to, and provide sequence information for, a different part of the genome. Similarly, data or sequence analysis techniques of the invention may be adapted for comparing many copies of a similar, identical, or overlapping sequence in order to determine if one or more of the molecules being characterized (e.g., sequenced) contains a genetic abnormality of interest. It should be appreciated that a genetic abnormality may be any form of mutation (for example, a point mutation, a transition, a transversion, a duplication, a deletion, an inversion, a translocation, or any other form of mutation). In certain aspects of the invention, analytical methods also may be adapted to detect rare modified nucleic acids such as hyper- or hypo-methylated nucleic acids that may be associated with a disease.

Sample Capture

Any method that is suitable for isolating a threshold number of genome equivalents of one or more target molecules may be used in methods of the invention. In preferred embodiments, a specific hybrid capture method may be used. A hybrid capture method may involve using a capture probe to bind to a target nucleic acid. The bound product then may be isolated. In one embodiment, a capture probe may be bound to a solid surface thereby acting as an anchor for isolating a target molecule. In other embodiments, a capture probe may be modified in a manner that allows it to be isolated or purified from a sample. For example, a capture probe may biotinylated, attached to an antigen, attached to a magnetic particle, attached to a molecular weight marker, attached to a charged particle, attached to another particle or other molecular "hook" that can be used to isolate that capture probe and thereby isolate a target molecule that is hybridized to the probe.

In aspects of the invention, a nucleic acid preparation is captured by repeated exposure of a biological sample (for example, a processed biological sample) to a capture probe on a solid support or in a medium, for example, by the rapid flow of the sample past a capture probe for the target nucleic acid molecule. The repetitive nature of such a method allows for a target molecule to bind and enhances the total number of molecules bound to the capture probe, providing a high yield capture. The solid support may be an electrophoretic medium (e.g., gel or beads) and the repetitive exposure of the sample to the capture probe may involve exposure to repeated cycles of electrophoresis in alternate directions (back and forth across a solid support region containing one or more different types of capture probe).

In some aspects, a sample is added to a portion of an electrophoretic medium having at least two regions arranged consecutively in a first spatial dimension. In some aspects, at least one of the at least two regions includes a first capture probe which is immobilized within that region. In some embodiments, one of the regions comprises an electrophoretic support (e.g., a gel such as a polyacrylamide gel, agarose gel, etc., or any combination thereof). In some embodiments, the second region may be a buffer (e.g., an electrophoretic buffer). In some embodiments, an electrophoretic support may be flanked on both sides by a buffer (e.g., the same buffer). In some embodiments, an electrophoretic support may include a single type of capture probe. In some embodiments, an electrophoretic support may include two or more (e.g., 2, 3, 4, 5, 6, 7, 8, 9, 10, about 15, about 20 or more) different capture probes. In some embodiments, a capture device or technique may involve capturing a plurality of different nucleic acids using different capture probes (e.g., 1, 2, 3, 4, 5, 6, 7, 8, 9, 10, about 15, about 20 or more) wherein each capture probe is immobilized on a separate electrophoretic support (e.g, a gel such as a polyacrylamide gel, agarose gel, any other suitable electrophoretic medium, etc., or any combination thereof). An electric field may be applied to the electrophoretic medium or support in a first direction which is parallel to the first dimension. An electric field may then be applied to the electrophoretic medium or support in a second direction which is opposite to the first direction. In further aspects, the electric field is applied repeatedly in each direction (e.g., about 2, 3, 4, 5, 6, 7, 8, 9, 10, 11, 12, 13, 14, 15, 20, 25, 50, or more times). For further details see for example U.S. Application No. 60/517,623 (pending) and U.S. application Ser. No. 10/982,733 (pending), the entire contents of which are incorporated herein by reference.

It should be appreciated that in some embodiments the capture probe(s) may be immobilized on a support or medium that is located within a medium such as a gel. However, in some embodiments, the capture probe(s) may be immobilized on a medium or support that may be disposed within a buffer (e.g., within a membrane or other support structure that may be disposed within a buffer such as an electrophoretic buffer).

In aspects of the invention, a sample may be exposed repeatedly to a capture probe using chromatographic methods, for example high performance liquid chromatography (HPLC), fast performance liquid chromatography (FPLC), etc.

In some embodiments, the captured sample may be amplified using PCR (or other amplification technique) to obtain a pool of DNA of an expected size. However, amplification is not required as the invention is not limited in this respect.

In some aspects of the invention, a capture probe may be any molecule capable of binding a target molecule (or a non-target molecule as described below). According to the invention, a target molecule is a molecule that contains a region suspected of being altered or mutant in disease (e.g., in adenomas or early stage cancers). Accordingly, a capture probe binds to a portion of a nucleic acid that is adjacent to (or overlaps) a position or region suspected of being mutant or altered. The capture probe should bind sufficiently close to the suspected position or region to effectively capture a significant number of target molecules that contain the suspected position or region. For example, in one embodiment the capture probe should bind to a portion of a nucleic acid that is within 5,000 bases (e.g., within 2,500 bases, within 1,000 bases, within 750 bases, within 500 bases, within 250 bases, or within 100 bases) of the position or region suspected of being mutated or altered. A capture probe may be between about 30 and about 40 bases long (e.g., about 31, 32, 33, 34, 35, 36, 37, 38, or 39 bases long). A capture probe may be between about 40 and about 50 bases long, between about 50 and about 75 bases long, or between about 75 and about 100 bases long. However, shorter or longer capture probes may be used. In some aspects, a capture probe selectively binds to a target molecule in a sample. In some embodiments, a capture probe is complementary to a region outside of a region of a nucleic acid to be amplified. In certain embodiments, a capture probe is complementary to a region within a region of a nucleic acid to be amplified. It should be appreciated that a capture probe may bind to target nucleic acid molecules with overlapping sequences, because nucleic acid fragmentation (e.g., resulting from natural fragmentation or exposure to a fragmentation technique) typically generates overlapping fragments of different sizes.

According to aspects of the invention, the capture probe can bind a target molecule during electrophoresis under appropriate conditions, such as pH, temperature, solvent, ionic strength, electric field strength etc. One of ordinary skill in the art would be able to adjust any condition as required to achieve optimal binding. A capture probe may include, but is not limited to, one or more peptides, proteins, nucleic acids, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, and/or monosaccharides.

When a nucleic acid capture probe is used (e.g., an oligonucleotide, a DNA, an RNA, a PNA, or other form of natural, synthetic, or modified nucleic acid) it should have a sequence that is sufficiently complementary to a portion of the target nucleic acid to bind specifically to the target nucleic acid under the conditions used for capture. In some embodiments, the capture probe may have a sequence that is 100% complementary. However, in other embodiments, the sequence may contain a few non-complementary nucleotides (e.g., at the 3' or 5' end). It should be appreciated that a small number of non-complementary nucleotides may be non-complementary. For example, the capture probe may be between 80% and 100% complementary (e.g., about 85%, about 90%, or about 95% complementary) to a portion of one strand of a target nucleic acid. However, other degrees of complementarity may be used provided that the capture probes can capture a sufficient number of genome equivalents of a target nucleic acid with sufficient specificity for subsequent analysis. It should be appreciated that a capture probe may be complementary to either strand of a target nucleic acid of interest. It should be appreciated that aspects of the invention do not require a pure sample of target nucleic acids. Nucleic acids other than the target nucleic acids may be isolated and included in the analytical step provided that they do not interfere with the sequence analysis in a way that would reduce the significance of the results to a level that falls below a predetermined level of statistical significance.

In some aspects of the invention, two or more capture probes may be provided. In some aspects, one or more of the capture probes bind to a target molecule. In some aspects, a plurality of different capture probes are used to capture different target nucleic acid molecules (e.g., 2 to 50, 5 to 40, or about 10, 15, 20, 25, 30, or 35 different target nucleic acid molecules). Each different target molecule may be from a different region of a genome, and each different target molecule may be suspected of containing a mutation or alteration associated with a disease or disorder. In other aspects, one or more of the capture probes may bind to a non-target molecule. In further aspects, a capture probe may bind a single molecule or a complex of molecules.

In aspects of the invention, the flow rate of the sample (e.g., the rate of electrophoresis) can be adjusted to either increase or decrease the flow rate. The flow rate can be maintained as a constant flow rate or adjusted over the time that the sample is exposed to the binding partner. For example, the flow rate can begin fast for a set period of time and then decreased at a certain time point. The flow rate can be decreased to a constant rate or to a sequentially decreasing flow rate.

In aspects of the invention, a sample may be a biological sample. A biological sample may be, but is not limited to, stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin. A sample also may be a pooled sample containing biological material and or isolated nucleic acids from a plurality of subjects (e.g., 2, 3, 4, 5, about 10, or more).

In aspects of the invention, a large amount of sample may be processed in order to increase the confidence level of isolating or capturing a rare event indicative of very early stage disease (e.g., an adenoma, an early stage cancer, etc.). For example, about 1 g, about 5 g, about 10 g, about 20 g, about 30 g, about 40 g, about 50 g, about 60 g, about 70 g, about 80 g, about 90 g, about 100 g, about 150 g, about 200 g, or more stool sample may be processed using a capture technique described herein. However, it should be appreciated that smaller or larger amounts of stool may be used.

In embodiments of the invention, exposure of a biological sample (for example a crude preparation of total nucleic acid from a biological sample) to immobilized capture probe(s) may be repeated between 2 and 100 times, e.g., between about 5 and about 50 times, between about 10 and about 40 times, or about 11, 12, 13, 14, 15, 16, 17, 18, 19, 20, etc. times, including about 25, 30, or 35 times.

A captured preparation of target nucleic acid molecules (e.g., of low genomic complexity) may be eluted using any suitable technique and prepared (e.g., single stranded molecules may be prepared) for subsequent analysis using a technique for analyzing nucleic acid samples of high genomic complexity. Sample capture techniques described herein may be used to analyze DNA and/or RNA.

Analysis of Captured Sample

Aspects of the invention may include analyzing a predetermined number of genome equivalents of one or more target nucleic acids in order to determine whether one or more of the individual target nucleic acid molecules contains an abnormal sequence.

In aspects of the invention, the presence of a low frequency altered/mutant target nucleic acid molecule in a captured preparation of target nucleic acid molecules of low genomic complexity may be detected using a technique that was designed for analyzing nucleic acid samples of high genomic complexity. In some aspects of the invention, methods for sequencing whole genomes or substantial portions thereof (e.g., chromosomes or significant portions thereof) may be used to detect low frequency events in a nucleic acid sample of low genomic complexity.

High complexity analytical techniques may involve primer extension (e.g., single base extension or multiple base extension) or nucleic acid degradation techniques that can analyze large numbers of different template nucleic acid molecules (e.g., sequence or provide the identity of at least one nucleotide position in a template molecule). High complexity analytical techniques may involve the parallel and/or serial processing of a large number of different template nucleic acid molecules. High complexity analytical techniques may involve a parallel and/or serial analysis of single molecules (e.g., single nucleic acid molecule sequencing). In one aspect, a preparation of template molecules may be dispersed across a solid surface and individual molecules may be immobilized on the surface (e.g., a microscope slide or similar substrate). A high sensitivity analytical technique may be used to characterize each immobilized molecule individually. For example, primer extension reactions may be used to incorporate labeled nucleotide(s) that can be individually detected in order to sequence individual molecules and/or determine the identity of at least one nucleotide position on individual template nucleic acid molecules. Detection may involve labeling one or more of the primers and or extension nucleotides with a detectable label (e.g., using fluorescent label(s), FRET label(s), enzymatic label(s), radio-label(s), etc.). Detection may involve imaging, for example using a high sensitivity camera and/or microscope (e.g., a super-cooled camera and/or microscope).

Accordingly, a "high complexity analytical step" may be a process that can analyze nucleic acid preparations of high genomic complexity. According to the invention, a preparation of target nucleic acid molecules of low genomic complexity such as those described herein may be used as template molecules and processed using a high complexity analytical technique. According to the invention, a high complexity analytical technique may be used to detect rare mutant/altered nucleic acid molecules in a preparation of many similar (or identical) nucleic acid templates of low genomic complexity.

Examples of high complexity nucleic acid analytical techniques are described herein. Additional analytical techniques are known in the art. Suitable techniques may be selected by one of ordinary skill in the art using the teachings of the invention. According to the invention, a sufficient number of target molecules should be captured and analyzed. A sufficient number is a number that provides a statistically significant result (e.g., a confidence level of at least 80%, at least 90%, at least 95%, or at least 99% that a particular alteration or mutation is either present or absent from a biological sample being analyzed).

In one embodiment, a digital analysis (e.g., a digital amplification and subsequent analysis) may be performed on at least a sufficient number of molecules to obtain a statistically significant result. Certain digital techniques are known in the art, see for example, U.S. Pat. No. 6,440,706 and U.S. Pat. No. 6,753,147, the entire contents of which are incorporated herein by reference. Similarly, an emulsion-based method for amplifying and/or sequencing individual nucleic acid molecules may be used (e.g., BEAMing technology; International Published Application Nos. WO2005/010145, WO00/40712, WO02/22869, WO03/044187, WO99/02671, herein incorporated by reference).

In one embodiment, a sequencing method that can sequence single molecules in a biological sample may be used. Sequencing methods are known and being developed for high throughput (e.g., parallel) sequencing of complex genomes by sequencing a large number of single molecules (often having overlapping sequences) and compiling the information to obtain the sequence of an entire genome or a significant portion thereof. According to the invention, such methods, although designed for complex sequence analysis, may be particularly suited to sequence a large number of substantially identical molecules in order to identify the rare one(s) that contain a mutation or alteration.

High complexity analytical or sequencing techniques may involve high speed parallel molecular nucleic acid sequencing as described in PCT Application No. WO 01/16375, U.S. Application No. 60/151,580 and U.S. Published Application No. 20050014175, the entire contents of which are incorporated herein by reference. Other sequencing techniques are described in PCT Application No. WO 05/73410, PCT Application No. WO 05/54431, PCT Application No. WO 05/39389, PCT Application No. WO 05/03375, PCT Application No. WO 05/010145, PCT Application No. WO 04/069849, PCT Application No. WO 04/70005, PCT Application No. WO 04/69849, PCT Application No. WO 04/70007, and US Published Application No. 20050100932, the entire contents of which are incorporated herein by reference.

High complexity analytical or sequencing techniques may involve exposing a nucleic acid molecule to an oligonucleotide primer and a polymerase in the presence of a mixture of nucleotides. Changes in the fluorescence of individual nucleic acid molecules in response to polymerase activity may be detected and recorded. The specific labels attached to each nucleic acid and/or nucleotide may provide an emission spectrum allowing for the detection of sequence information for individual template nucleic acid molecules. In certain embodiments, a label is attached to the primer/template and a different label is attached to each type of nucleotide (e.g., A, T/U, C, or G). Each label emits a distinct signal which is distinguished from the other labels.

High complexity analytical or sequencing techniques may involve or be based on methods or technology described in Shendure et al., Nature Reviews/Genetics, Volume 5, May 2004, pages 335-344; Braslavsky et al., PNAS, Apr. 1, 2003, Volume 100, No. 7, pages 3960-3964; the entire disclosures of which are incorporated herein by reference.

In other embodiments, high complexity analytical or sequencing techniques may involve providing a primed target polynucleotide linked to a microfabricated synthesis channel, and flowing a first nucleotide through the synthesis channel under conditions such as to allow the first nucleotide to attach to the primer. The presence or absence of a signal is determined, the presence indicating that the first nucleotide was incorporated into the primer and the identity of the complementary base that served as a template in the target polynucleotide is determined. The signal is then removed or reduced and the process repeated with a second nucleotide. The second nucleotide can be either the same as the first nucleotide or a different nucleotide. The specific labels attached to each nucleic acid provide an emission spectra allowing for detection of sequence information of the nucleic acid molecule. In other embodiments, a plurality of different primed target polynucleotides linked to different synthesis channels is used. In further embodiments, the polynucleotide is attached to a surface. In some embodiments, a label is attached to the nucleotide.

In certain embodiments, a high complexity analytical or sequencing technique may be provided by Helicos BioSciences Corporation (Cambridge, Mass.) (US Published Application No.: 20060024711, incorporated herein by reference). Briefly, in some embodiments, single strands of purified DNA with a universal priming sequence at each end of the strand may be generated. The strands are labeled with a fluorescent nucleotide and hybridized to primers immobilized on a surface. The primer duplexes are analyzed and the positions of each duplex recorded. DNA polymerase and a fluorescently labeled nucleotide are added and bind the appropriate primers. The sample is washed to remove unbound nucleotides and excess polymerase. The samples are analyzed and the positions of the incorporated nucleotides recorded. The fluorescent label is removed and a second labeled nucleotide is added and the process is repeated. The process may be repeated several times until a desired length is reached.

Other useful genome/complex sequencing methods include high throughput sequencing using the 454 Life Sciences Instrument System (International Published Application No. WO2004/069849, filed Jan. 28, 2004). Briefly, a sample of single stranded DNA is prepared and added to an excess of DNA capture beads which are then emulsified. Clonal amplification is performed to produce a sample of enriched DNA on the capture beads (the beads are enriched with millions of copies of a single clonal fragment). The DNA enriched beads are then transferred into PicoTiterPlate™ and enzyme beads and sequencing reagents are added. The samples are then analyzed and the sequence data recorded. Pyrophosphate and luciferin are examples of the labels that can be used to generate the signal.

A label includes but is not limited to a fluorophore, for example green fluorescent protein (GFP), a luminescent molecule, for example aequorin or europium chelates, fluorescein, rhodamine green, Oregon green, Texas red, naphthofluorescein, or derivatives thereof. In some embodiments, the polynucleotide is linked to a substrate. A substrate includes but is not limited to, streptavidin-biotin, histidine-Ni, S-tag-5-protein, or glutathione-S-transferase (GST). In some embodiments, a substrate is pretreated to facilitate attachment of a polynucleotide to a surface, for example the substrate can be glass which is coated with a polyelectrolyte multilayer (PEM), or the polynucleotide is biotinylated and the PEM-coated surface is further coated with biotin and streptavidin.

In other embodiments, single molecule sequencing technology available from US Genomics, Mass., may be used. For example, technology described, at least in part, in one or more of U.S. Pat. Nos. 6,790,671; 6,772,070; 6,762,059; 6,696,022; 6,403,311; 6,355,420; 6,263,286; and 6,210,896 may be used.

Other sequencing methods, including other high complexity analytical techniques also may be used to analyze DNA and/or RNA according to methods of the invention. It should be appreciated that a sequencing method does not have to be a single molecule sequencing method. In one embodiment, a method that sequences small numbers of molecules (e.g., 2, 3, 4, 5, 6, 7, 8, 9, 10, to about 15 or about 20 molecules) in a single reaction may be useful if the results can reliably detect the presence of a single (or a small number) of abnormal nucleic acids amongst the number of molecules that are being sequenced. It should be appreciated that the entire sequence of a capture target molecule does not need to be determined. It is sufficient to determine the sequence at a position, on the target molecule, suspected of containing an abnormality. It also should be appreciated that the analytical method does not need to identify the actual sequence of each molecule. In some embodiments, it may be sufficient to detect the presence of a small number (e.g., one or two) or a small percentage (e.g., 10%, 5%, 1%, 0.1%, 0.01% or lower) of abnormal molecules in a sample. For example, certain physical characterizations (e.g., mass detection such as mass spectrometry) may be used to distinguish normal from abnormal molecules and detect the presence of a small amount of abnormal nucleic acids associated with a disease.

Adenomas

In one embodiment, aspects of the invention may be used to detect indicia of adenomas in a biological sample. According to aspects of the invention, detecting the presence of an adenoma may be useful for detecting early signs of cancer or precancer. Adenomas are typically glandular tumors or tumors of glandular origin. Adenomas may be early indicia of cancer, for example colon cancer. Not all adenomas become cancers. However, many cancers (e.g., carcinomas such as colorectal carcinomas) are thought to develop from adenomas. Indeed, a majority of colon cancers are thought to develop from adenomas. Therefore, detecting adenomas is particularly useful for identifying early signs or risks of colorectal cancer (e.g., cancerous and precancerous lesions or growths in the colon).

Adenomas may be invasive adenocarcinomas, significant adenomas, and low potential polyps. Invasive adenocarcinomas may be, for example, adenocarcinomas at different TNM stages (e.g., TNM stages 1, 2, 3, or 4). Significant adenomas may be, for example, carcinomas in-situ/high-grade dysplasias (CIS/HGD) having a diameter of greater than 1 cm, about 1 cm, less than 1 cm, or of unknown size; villous adenomas having a diameter of greater than 1 cm, about 1 cm, less than 1 cm, or of unknown size; tubulovillous adenomas having a diameter of greater than 1 cm, about 1 cm, less than 1 cm, or of unknown size, and low-grade dysplasias (LGD) with a diameter of greater than or equal to 1 cm. Low potential polyps may be, for example advanced polyps, and adenoma low-grade dysplasias (LGD) with an unknown diameter or a diameter of less than 1 cm. Aspects of the invention may be useful to detect any one or more of these different types of adenomas.

According to aspects of the invention, adenomas can be detected at different positions in the colon and rectum (including the right and left colon and the transverse colon).

Accordingly, appropriate capture probes may be used to capture target nucleic acid molecules that contain one or more of the above regions of interest. Similarly, appropriate analytical or sequencing primers (e.g., primers between about 10 and about 40, or about 15 and about 30 bases long) may be used to interrogate these regions for the presence of a mutant or altered nucleotide associated with an adenoma.

Similarly, other combinations of one or more of these and/or other genomic region(s) associated with adenomas or early stage cancer may be captured and interrogated for the presence of these or other known mutations or alterations associated with adenoma and or cancer (e.g., colorectal adenoma or cancer).

Examples of Genetic Loci and Genetic Abnormalities

In one embodiment, the following panel may be used to detect adenomas (or other growths, tumors, cancers or precancers, etc.) with greater than 60% sensitivity: assays are performed to detect one or more genetic abnormalities from a multiple mutation panel of genetic abnormalities at 22 loci including KRas (Thor, A. et al., 1984, Nature, 311(5986):562-5) mutations in codon 12 (KRas codon 12 position 1, KRas codon 12 position 2) and codon 13 (KRas codon 13 position 2); mutations in familial adenomatous polyposis gene (APC; Ashton-Rickardt P. G. et al., 1989, Oncogene, 4(10):1169-74) codons 1309 (deletions), 1306 (mutations at position 1), 1312 (mutations at position 1), 1367 (mutations at position 1), 1378 (mutations at position 1), 1379 (mutations at position 1), 1450 (mutations at position 1), 1465 (deletions), 876 (mutations at position 1) and 1554 (insertions); mutations in P53 (Hinds P. W. et al., 1990, Cell Growth Differ., 1(12):571-80) codons 175 position 2, 245 position 1, 245 position 2, 248 position 1, 248 position 2, 273 position 1, 273 position 2 and 282 position 1; and deletions at the BAT-26 (Iwaya, T. et al., 1998, Genes Chromosomes Cancer, 23(4):317-22) locus. This panel is referred to herein as the V1 panel. Mutations at these loci can be detected using primer extension assays (including single base extension assays and assays designed to detect BAT-26 deletions) or other assays that are useful to detect one or more of these genetic abnormalities.

In another embodiment, the following panel may be used to detect adenomas (or other growths, tumors, cancers or precancers, etc.) with greater than 60% sensitivity: assays are performed to detect hypermethylation at one or both of the helicase-like transcription factor (HLTF; US Published Application No.: 20040242510, incorporated herein by reference in its entirety) and vimentin (V29; US Published Application No.: 20050106593, incorporated herein by reference in its entirety) loci. Hypermethylation at these loci can be detected using methylation specific primer analysis (e.g., MSP amplification) or other assays that are useful to detect hypermethylation at one or more of these genetic loci.

In one embodiment, scanning for one or more mutations at the APC-MCR may detect adenomas (or other growths, tumors, cancers or precancers, etc.) with greater than 74% sensitivity.

In one embodiment, the following panel may be used to detect adenomas (or other growths, tumors, cancers or precancers, etc.) with greater than 90% sensitivity: scanning for one or more mutations in the APC-MCR locus, exon 9 of the PIK3CA (Shayesteh, L. et al., 1999, Nature Genetics, 21(1):64-5) locus, exon 20 of the PIK3CA locus, B-catenin (US Published Application No.: 20020086386, e.g., exon 5), or a mutation in BRAF (US Published Application No.: 20030224993) that results in a V599E amino acid change. Scanning as described herein can be used to detect one or more mutations in the APC-MCR locus, exon 9 of the PIK3CA locus, or exon 20 of the PIK3CA locus. Mutations at the BRAF locus can be detected via primer extension or other appropriate methodology.

In one embodiment, a combination of all of the above loci may be used to detect adenomas (or other growths, tumors, cancers or precancers, etc.) with a greater than 95% sensitivity (e.g., greater than 98% sensitivity).

Other Genetic Loci and Genetic Abnormalities Associated with Disease

Aspects of the invention may be used to detect the presence of a genetic abnormality in any one or more loci of interest that may be associated with a disease. For example, one or more different loci associated with an adenoma, a tumor, a cancer, a precancer or any other disease or disorder may be assayed according to methods of the invention. Examples of target nucleic acids include, but are not limited to, one or more oncogenes, tumor suppressor genes, genomic regions containing nucleic acid repeats (e.g., different forms of satellite DNA such as micro or mini satellite DNA), other genetic loci (coding or non-coding genetic loci), or combinations thereof.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety to the extent that they are not contradictory with the present teachings.

EXAMPLES

Example 1

The following example illustrates a method for preparing a DNA sample from a stool sample, see for example US Published Application No. 20040043467 and US Published Application No. 20040014104, the entire contents of which are incorporated herein by reference.

A stool sample is collected and may be stored at −80° C. before use. The sample is thawed and resuspended in buffer, for example 10 mM Tris-Cl pH 8.0, 1 mM EDTA and 150 mM NaCl, or other suitable buffer as known to those of ordinary skill in the art. In one embodiment, the buffer may contain between 100 mM and 200 mM EDTA, for example about 150 mM EDTA. A suitable ratio of buffer to sample may be used, for example between 5:1 and 20:1 (mls/g of sample), for example about 7:1. The sample is then homogenized utilizing an EXACTORU™ stool shaker (EXACT Laboratories Marlborough, Mass.). Following homogenization, the stool sample is centrifuged to remove all particulate matter, and the supernatants are incubated at 37° C. Proteinase K (0.5 μg/μL) and SDS (0.5%) may be added at this point. The DNA is extracted from the supernatant using Tris saturated phenol (Gibco/BRL, Grand Island, N.Y.), phenol/chloroform/isoamyl alcohol (25:24:1), and chloroform. The DNA is then precipitated (1/10 volume 3M NaAc and an equal volume isopropanol), removed from solution by centrifugation, and resuspended in TE (0.01M Tris pH 7.4, 0.001M EDTA) buffer containing RNase A (2.5 μg/4), or other suitable buffer.

Example 2

The following example illustrates methods and devices useful for capturing a sample by repeated exposure to a capture probe. In the following example a capture probe is referred to as a binding partner.

All technical and scientific terms used herein, unless otherwise defined below, are intended to have the same meaning as commonly understood by one of ordinary skill in the art. References to techniques employed herein are intended to refer to the techniques as commonly understood in the art, including. variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "target molecule" means any molecule of interest in a sample that is desired to be detected, separated, isolated, or enriched relative to, non-target molecules within the test sample. Target molecules can include, without limitation, proteins, peptides, nucleic acids, amino acids, nucleosides, antibodies, antibody fragments, antibody ligands, aptamers, peptide nucleic acids, small organic molecules, lipids, hormones, drugs, enzymes, lectin, cell adhesion molecule, antibody epitope, enzyme substrates, enzyme inhibitors, coenzymes, inorganic molecules, polysaccharides, monosaccharides. A sample can include more than one target molecule such that the methods of the invention are used to simultaneously or sequentially separate, isolate, enrich or detect more than one target molecule in a sample. A sample can also include cells expressing target molecules and can be isolated by the methods of the invention.

As used herein, the term "non-target molecule" means any molecule in a sample that is not a target molecule.

As used herein, the term "binding partner" means any molecule which has selective binding affinity for a target molecule or non-target molecule and, therefore, can bind the target molecule during electrophoresis under appropriate conditions (e.g., pH, temperature, solvent, ionic strength, electric field strength). Binding partners can include, without limitation, proteins, peptides, nucleic acids, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, and monosaccharides.

As used herein, the term "selective binding affinity" means greater affinity for non-covalent physical association or binding to selected molecules relative to other molecules in a sample under appropriate conditions. Examples of selective binding affinity include the binding of polynucleotides to complementary or substantially complementary polynucleotides, antibodies to their cognate epitopes, and receptors to their cognate ligands under appropriate conditions (e.g., pH, temperature, solvent, ionic strength, electric field strength). Selective binding affinity is a relative term dependent upon the conditions under which binding is tested, but is intended to include at least a 2× greater affinity for target molecules than any non-target molecules present in a sample under appropriate conditions. If a test sample includes more than one type of target molecule (e.g., allelic variants from one locus), a binding partner can have selective binding affinity for one or more of the different target molecules relative to non-target molecules.

As used herein, the term "substantially complementary" means having a nucleotide sequence that has sufficient identity to a sequence that is perfectly complementary to a specified polynucleotide to have selective binding affinity for that specified polynucleotide under appropriate conditions.

As used herein, the term "antibody" means any isolated naturally-produced antibody, recombinantly-produced antibody, monoclonal or polyclonal antibody, synthetic antibody such as a chimeric antibody, or any antibody fragment such as an Fab fragment, F(ab')2 fragment, Fv fragment, or single-chain Fv fragment (scFv).

As used herein, the term "aptamer" means any polynucleotide having selective binding affinity for a non-polynucleotide molecule via non-covalent physical interactions. An aptamer is, a polynucleotide that binds to a ligand in a manner analogous to the binding of an antibody to its epitope.

As used herein, the terms "opposite" and "reverse" and "backward", when referring to the direction of electrophoresis, mean a substantially anti-parallel direction relative to a previous direction of electrophoresis. The opposite, reverse or backward direction need not be rotated exactly 180° in the plane of electrophoresis. Rather, a substantially opposite, reverse or backward rotation may be employed (e.g., rotation through 120°-240°) such that the test sample is moved in an oblique manner as in transverse alternating field electrophoresis (TAFE) and contour-clamped homogeneous electric field (CHEF) electrophoresis (see, e.g., Gardiner et al. (1986), *Somatic Cell Molec. Genet.* 12:185-195; Chu et al. (1986), *Science* 234:1582-1585).

As used herein, the terms "detectable" and "labeled" mean chemically constituted or modified to facilitate detection by standard chemical, biochemical, or biological assays including, but not limited to, radioimmunoassay (e.g., radioactive isotope assays), photospectrometric assays (e.g., fluorescence, chemiluminescence, bioluminescence assays), immunoassays (e.g., enzyme-linked immunosorbent assays (ELISA), sandwich assays, immunofluorescence assays, immunoradio assays), hybridization assays (e.g., labeled oligonucleotide hybridization or displacement assays), plasmon resonance assays (e.g., BiaCORE™ BiaCORE™ assays (Amersham-Pharmacia, Piscataway, N.J.)), nucleic acid amplification assays (e.g., PCR assays, LCR assays), and the like.

As used herein, unless specifically indicated otherwise, the word "or" is used in the inclusive sense of "and/or" and not the exclusive sense of "either/or"

As used herein, the terms "increase" and "decrease" mean, respectively, a statistically significantly (i.e., $p<0.1$) increase or decrease.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values >0 and <2 if the variable is inherently continuous.

The following sections provide additional embodiments that may be useful for hybrid capture using electrophoresis.

Electrophoretic Media

Electrophoretic media useful in the invention include any media through which charged molecules can migrate in solution in response to an electric field and to which binding partners can be immobilized, including polymeric matrices of gels, packed volumes of particles or beads, and hybrid media including beads or particles embedded in a polymeric gel matrix.

In some embodiments, one or more regions of the electrophoretic medium can be formed from different materials than the other regions (e.g., different polymeric matrices, different packed beads, hybrid gel-bead media, and combinations thereof). The materials for the different regions can be selected according to principles well known in the art to effect different separations or to selectively retain target or non-target molecules.

A. Polymeric Gel Media

In some embodiments, one or more of the regions of the electrophoretic medium are formed as a polymeric gel. Commonly used gel media useful in the invention include polymeric gels formed from monomers of acrylamide, agarose, starches, dextrans, and celluloses, as well as chemically modified or functionalized variants of these monomers (see, e.g., Polysciences, Inc., Polymer & Monomer catalog, 1996-1997, Warrington, Pa.), (Smithies (1959), *Biochem. J.* 71:585; Quesada (1997), *Curr. Opin. Biotech.* 8:82-93).

For the separation of proteins, 5-15% (w/v) polyacrylamide gels are typically used. For small nucleic acid molecules (e.g., <1 kb), 5%-20% (w/v) polyacrylamide gels can be used. For the separation of very large nucleic acid fragments, however, the pore size of standard polyacrylamide gels can be insufficient to allow adequate movement and separation of the fragments. Therefore, lower percentage polyacrylamide gels (e.g., 2-5% (w/v)) can be used. These low percentage polyacrylamide gels, however, have poor mechanical strength. Alternatively, agarose electrophoretic media can be used for nucleic acid gels. For example, gels of 0.5-2.0% (w/v) agarose can be for most nucleic acid separations, and 0.5-1.0% (w/v) gels can be used for larger nucleic acid fragments. Low percentage agarose gels have greater mechanical strength than low percentage polyacrylamide gels.

For some methods, composite gel media containing a mixture of two or more supporting materials can be used. For example, and without limitation, composite acrylamide-agarose gels can be employed which contain from 2-5% (w/v) acrylamide and 0.5%-1.0% (wfv) agarose. In such gels, the polyacrylamide matrix performs provides the major sieving function, whereas the agarose provides mechanical strength for convenient handling without significantly. altering the sieving properties of the acrylamide. In composite gels, the binding partners optionally can be attached to the component that performs the major sieving function of the gel, because that component more intimately contacts the target molecules.

In other embodiments, macroporous gels can be formed by mixing the gel-forming materials with organic liquids or pore-forming agents prior to polymerization. These liquids or pore-forming agents can be removed subsequent to polymerization to create a polymeric gel matrix with larger pores. The larger pores are useful for permitting the movement of large target molecules (e.g., genomic fragments) through the polymeric matrix material, while also maintaining the mechanical strength of the medium.

B. Packed Bead Media

In other embodiments, as an alternative to polymeric gel media, packed volumes of small beads or particle beds can be used as electrophoretic media. Such particle beds, which are frequently used in chromatography, have the advantage of large interstitial voids which allow for the passage of large molecules such as nucleic acid fragments>1 kb. In some embodiments, the beads have average diameters in the range of 1-5 µm, 5-50 µm, or 50-150 µm, although larger beads can also be used. Beads useful in the invention can be formed from materials including, but not limited to, agarose polymers, dextran polymers, acrylic polymers, glass, latex, polystyrene, poly(hydroxyethylcellulose), poly(ethylenoxide), a modified acrylamide, and acrylate ester.

Beads useful in the invention can be solid beads or porous beads, In some embodiments, porous beads will have diameters in the range of 10-20 µm or, more generally 10-50 µm, and can have a wide range of pore sizes. Such porous beads can include binding partners embedded within the pores and/or bound to the surfaces of the probes. Non-porous or solid beads can have a wider range of diameters, including without limitation beads in the range of 1-100 µm.

Such beads conveniently can be coated (including the interiors of pores) with one member of an affinity binding pair such that binding partners bound to the other member of the affinity binding pair can be immobilized on the beads. For example, and without limitation, beads can be coated with avidin or streptavidin and binding partners can be conjugated to biotin to cause immobilization of the binding partners on the beads. Similarly, probes can be coated with Protein A to immobilize antibody binding partners that bind to Protein A.

Beads also can be treated or coated to reduce non-specific binding or target or other molecules in a sample. For example, beads can be treated to reduce the number of hydrophobic groups (e.g., benzyl groups) on the surface, or to increase the number of hydrophilic groups (e.g., carboxyl groups) on the surface. Beads can also be coated with gelatin, bovine serum albumin or other molecules that will non-specifically bind to and "block" the surface prior to use with test samples.

In embodiments employing beads as electrophoretic media, it may be necessary to separate different regions of the electrophoretic medium by separators which are membranes or meshes that prevent the movement of the beads from one region to another in response to the electric field. Such separators must have pores sufficiently large to be permeable to the target molecules, but not permeable to the beads. Such separators can be used alone, or in combination with spacer elements or other structures between regions of the electrophoretic medium.

C. Hybrid Gel-Bead Media

In other embodiments, hybrid media can be formed which include small beads or particles embedded or enmeshed in a polymeric gel. Such hybrid-gel media can be formed from any of the polymeric gel materials and any of the bead materials described above. For example, and without limitation, polyacrylate or polystyrene beads can be embedded in a polyacrylamide or agarose gel matrix. In some embodiments, the binding partners will be bound to the beads prior to production of the hybrid gel-bead media. In other embodiments, however, the binding partners can be co-polymerized into the polymeric gel during its formation, or can be bound to the hybrid gel-bead media after formation.

D. Electrophoretic Conditions

Appropriate conditions for electrophoresis, including buffer systems, temperature, and voltage, can be chosen by those of skill in the art, according to well known principles, depending upon the type of test sample and target molecules being assayed and the type of electrophoretic medium being employed.

For example, because the target molecules must be charged in order to migrate in an electric field, buffers of suitable pH are chosen such that the target molecules are appropriately charged during electrophoresis. In some embodiments, the buffers can be varied during or between electrophoretic steps or cycles in order to alter the charges of the target or non-target molecules and thereby affect electrophoretic separation. In addition, buffers can be chosen which promote greater or lesser degrees of stringency or selectivity of affinity binding to the binding partners. In certain embodiments, the buffers in each region of the apparatus may be different buffer or the same buffer. For example, when attempting to capture all alleles of a given gene with a single polynucleotide binding partner, a lesser degree of stringency can be employed than when attempting to capture only a specific allele which differs from other alleles by a single nucleotide polymorphism.

Similarly, the electrophoretic medium can be maintained at a chosen temperature to prevent denaturation of biomolecules (e.g., <37° C.) or to promote denaturation (e.g., 60° C.-90° C.). In some embodiments, the temperature can be varied during or between electrophoretic steps or cycles in order to alter the binding of the target or non-target molecules and thereby affect electrophoretic separation. For example, when attempting to capture all alleles of a given gene with a single polynucleotide binding partner, a lower temperature can be employed than when attempting to capture only a specific allele which differs from other alleles by a single nucleotide polymorphism.

Similarly, the electric field across an electrophoretic medium can be chosen according to principles well known in the art. In particular, voltages are chosen which cause a current which allows the target molecules to migrate amongst regions in a reasonable period of time without causing substantial temperature increases in the medium which might disrupt either the target molecules or the medium itself. Typically, for protein electrophoresis in an SDS-polyacrylamide gel, currents of 2-20 mA can be used, whereas for agarose gel electrophoresis of nucleic acids, a current of 100-200 mA can be used.

Electrophoretic Apparatus

Figure 2:
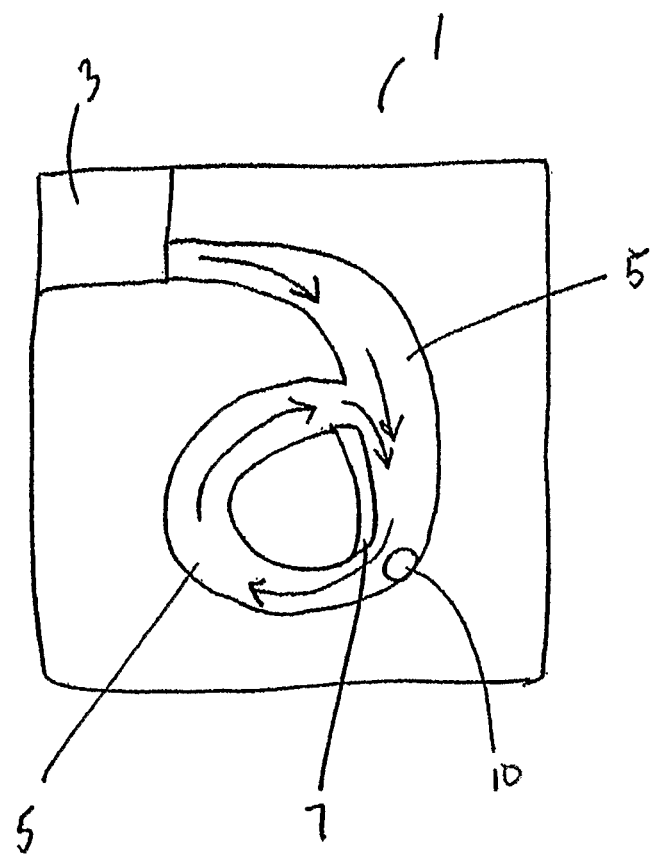
FIG. 2 is a schematic representation of an embodiment of the methods of the invention performed in a solid support having a channel.

In one aspect, the present invention provides a cartridge for use in methods for separating target molecules from non-target molecules in a sample. By way of example and as illustrated in, FIG. 2, the cartridge 1 has a substantially planar housing, fabricated from a moldable material such as polystyrene or polycarbonate, or polyvinylchloride, defining at least one fluid inlet port 3 and at least one conduit 5 having a fluid contacting surface in fluid communication with the fluid inlet port 3. The cartridge 1 further comprises at least one binding partner disposed on a first region 7 of the fluid contacting surface of the conduit 5, so that when a sample is applied to the fluid inlet port 3, the sample traverses the region and target molecules in the sample bind to the binding partner during transport of the sample through the conduit 5. FIG. 2 illustrates an embodiment of the cartridge in which the conduit forms a loop through which the sample can repeatedly pass, thereby repeatedly contacting the binding partner for the target molecule. In an embodiment, at least one region comprises a binding partner for a non-target molecule. The cartridge may also comprise at least one additional port or vent 10 that attaches to a pump for circulating the sample or through which the sample can be removed or through which the target molecule can be eluted. Elution of the molecules bound to the binding partners in individual regions of the conduit may be performed separately such that several target molecules and/or non-target molecules are separated and/or isolated. In an embodiment, the regions of the cartridge can be separated (e.g., snapped apart) prior to the Elution step. In another embodiment, the regions of the cartridge can be isolated such that fluid communication is no longer possible between the regions and molecules bound in each region can be eluted and isolated separately.

Figure 3:
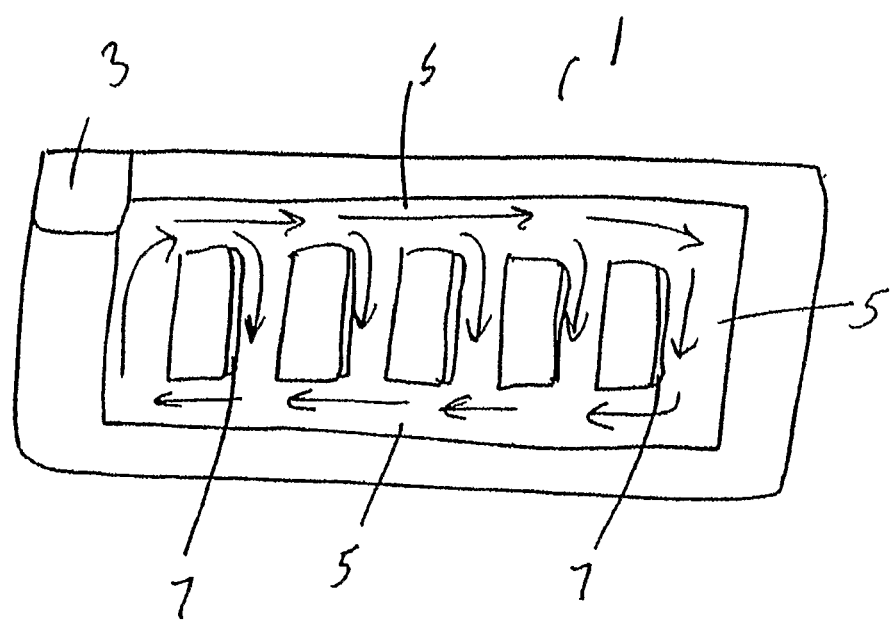
FIG. 3 is a schematic representation of an embodiment of the methods of the invention performed in a solid support having a plurality of channels.

Referring to FIG. 3, in another embodiment, the cartridge 1 comprises a fluid inlet port 3 and multiple conduits 5 in fluid communication with each other and at least one region 7 of the conduits contains a binding partner for a target molecule. The a sample can traverse the conduits and the target molecule binds to its binding partner, which are bound to regions of the conduits. Multiple conduits are useful for increasing the surface area to which binding partners for target molecules are bound or for having several regions containing different binding partners for different target molecules and/or non-target molecules. In an embodiment, at least one region contains a non-target molecule. The cartridge may also have at least one additional port or vent for attaching to a pump or through which the sample can be removed or through which the target molecule can be eluted. Elution of the molecules bound to the binding partners in individuals regions may be performed separately such that several target molecules and/or non-target molecules are separated and/or isolated. In an embodiment, the regions or conduits of the cartridge can be separated (e.g., snapped apart) prior to the elution step. In another embodiment, the regions of the cartridge can be isolated such that fluid communication is no longer possible between the conduits or regions and molecules bound in each region can be eluted and isolated separately.

Figure 4:
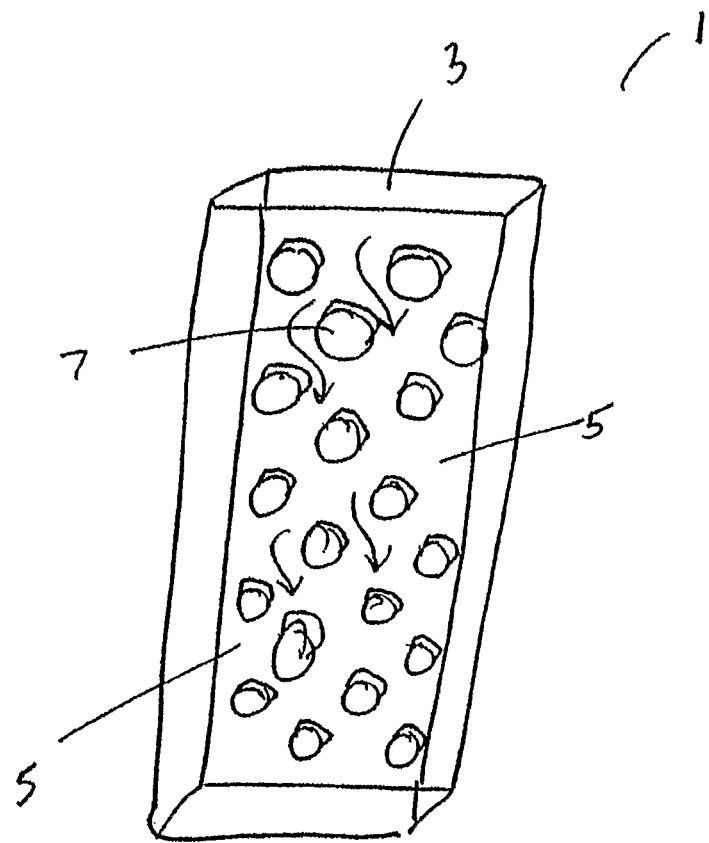
FIG. 4 is a cross section of a solid support used in the practice of the methods of the invention.
Figure 5:
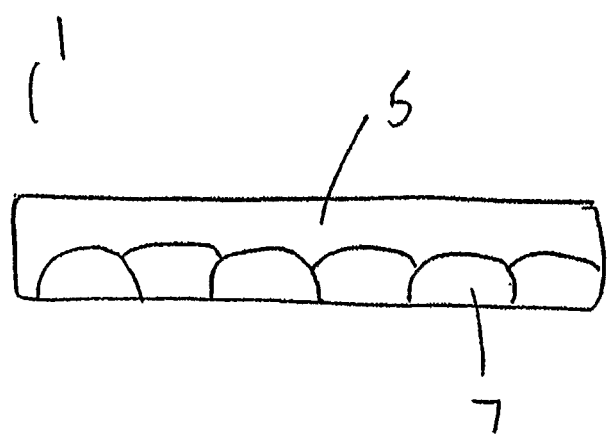
FIG. 5 is a schematic representation of the cross-section shown in FIG. 4.

Referring to FIG. 4, in another embodiment, the cartridge 1 comprises a fluid inlet port 3 and at least one conduit 5 in fluid communication with the fluid inlet port 3 and at least one region of the conduit that comprises at least one projection 7 containing a binding partner for a target molecule. Projections protrude into the conduit such that target molecules flows into and around the projection and provide additional surface area for binding partners for target molecules, thereby increasing the opportunity of the target molecule to bind to its binding-partner. In an embodiment, the projections are staggered as shown in FIG. 4. The projection may be any shape, e.g., may be rounded, flat, or square, for example. FIG. 5 illustrates a cross section of an embodiment of the embodiment of FIG. 4, showing the projections 7 with in the conduit 5. In an embodiment, for example, the sample can be pulled along the conduit to via positive or negative pressure induced by a pump connected to a pump port located up stream or downstream of the region containing the binding partner. The pumps may be alternated such that the sample passes back and forth over the binding 5 partner region. Alternatively, a manual system may be used, such as, for example, two syringes attached to either end of the cartridge, in which the sample is repeatedly pulled or pushed past the regions of the conduit comprising the binding partner, using positive or negative pressure of the syringes. Fluid flow through the cartridge is achieved, for example, by the methods described, in U.S. Pat. No. 6,287,850. In an embodiment of the invention the cartridge is a microchip or wafer, and binding partner arrays are prepared, for example, as described in U.S. Pat. No. 5,143,854 or PCT WO 92/10092. The chip may be composed of a wide range of material, either biological, nonbiological, organic, inorganic, or a combination of any of these, existing as particles, strands, precipitates, gels, sheets, tubing, spheres, containers, capillaries, pads, slices, films, plates, slides, etc. The chip may have any convenient shape, such as a disc, square, sphere, circle, etc. The chip is preferably flat but may take on a variety of alternative surface configurations. For example, the chip may contain raised or depressed regions on which a binding partner is located. The chip and its surface preferably form a rigid support on which the binding partner can be formed. The chip may be a polymerized Langmuir Blodgett film, functionalized glass, Si, Qe, GaAs, GaP, SiO2, SiN4, modified silicon, or any one of a wide variety of gels or polymers such as (poly)tetrafluoroethylene, (poly)vinylidenedifluoride, polystyrene, polycarbonate, or combinations thereof. Other materials with which the chip can be composed of will be readily apparent to those skilled in the art upon review of this disclosure as well as U.S. Pat. Nos. 6,287,850, 6,399,365, 6,551,817, 6,664,104, 6,653,121, and 6,664,104, the entire disclosures of which are incorporated herein by reference. In a preferred embodiment, the chip is flat glass or single-crystal silicon, The surface of conduit within the chip maybe composed of the same material as the wafer and may be composed of any of a wide variety of materials, for example, polymers, plastics, resins, polysaccharides, silica or silica-based materials, carbon, metals, inorganic glasses, membranes, or any of the above-listed wafer materials.

In another aspect, the invention provides methods of preparing the cartridge by drying a binding partner onto the surface of at least a portion of one conduit of the cartridge. Drying of the binding partner is accomplished by applying a volume of a mixture comprising a binding partner of interest onto the surface of at least a portion of at least one conduit. The binding partner used will depend upon what the cartridge will be used to assay for. The binding partner may be permanently bound to the conduit or may be reversibly bound to the conduit according to art known methods.

Target Molecules and Test Samples

The target molecules to be separated, isolated, enriched or detected by the methods of the present invention include any charged biomolecules which are capable of separation by electrophoresis in an appropriate buffer. Such target molecules include, without limitation, nucleic acids, such as genomic DNA, cDNA, mRNA or amplified DNA/RNA products, small polypeptides such as certain hormones and proteolytic fragments, and larger polypeptides such as secreted proteins, structural proteins, receptors, enzymes, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, monosaccharides. In addition, the target molecules can be specific allelic variants of these molecules, such as mutant or disease-associated forms, or allelic variants which are useful in forensic identifications. In some embodiments, there will be a single type of target molecule (e.g., a nucleic acid having a specific nucleotide sequence), whereas in other embodiments the target molecules can comprise a class of molecules (e.g., nucleic acids of varying lengths including a specific nucleotide sequence, or nucleic acids corresponding to various alleles of a particular gene).

Test samples which can be used in the present invention include any samples which include target biomolecules which can be separated, isolated, enriched or detected by the methods of the invention. Such test samples include, without limitation, bodily fluids, excreta and tissue samples. For example, stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin can all be used as sources for test samples. In addition, test samples for environmental testing (e.g., detection of pathogens in water supplies) and industrial or commercial process controls (e.g., meat and poultry processing) can be used. For example, and without limitation, test samples can be obtained from ponds, streams or rivers, watersheds, municipal water supplies, water treatment facilities, meat and poultry slaughterhouses or processing plants, food processing factories, pharmaceutical and biologics manufacturing facilities, blood banks, organ banks and the like. Test samples can also be obtained from sites of potential contamination with dangerous pathogens or biomolecules, including sites of possible biological or chemical weapons use.

In some embodiments, test samples can be directly applied to an electrophoretic medium. In other embodiments, however, the raw samples are subjected to standard sample preparation techniques, optionally including partial purification, which render the target molecules more accessible to binding partners during electrophoresis. For example, and without limitation, blood samples can be centrifuged to separate fractions including whole cells or membranes from serum, feces samples can be sectioned and homogenized with physiologically acceptable buffer and detergent (see, e.g., U.S. Pat. No. 5,741,650, U.S. Pat. No. 6,503,718), and sputum samples can be liquefied and fractionated. Antibiotics or bactericides optionally can be added to samples to prevent further growth of any organisms present. Whole cells can be removed or can be lysed to release their contents. For assays in which nucleic acids are to be detected, proteinases and inhibitors of DNA and RNA degrading enzymes optionally can be added. In addition, target molecules which are nucleic acids optionally can be amplified prior to detection. Alternatively, for assays in which proteins are to be detected, inhibitors of proteinases optionally can be added. Nucleic acids in test samples can be sheared or cut into smaller fragments (e.g., by mechanical shearing or restriction enzyme digestion), or can be amplified prior to electrophoresis by methods known in the art including, but not limited to, the polymerase chain reaction (PCR) and ligase chain reaction (LCR). Heterogeneous samples can be purified to remove substantially all non-nucleic acid molecules or substantially all non-protein molecules prior to loading the test sample into the electrophoretic medium. For example, and without limitation, nucleic acid samples can be extracted with phenol and chloroform. Many other standard techniques of nucleic acid and protein sample preparation are known in the art and can be found in, for example, Sambrook et al., eds., *Molecular Cloning: A Laboratory Manual*, 3rd Ed., Cold Spring Harbor Laboratory Press, Cold Spring Harbor, N.Y. (2001), and Watson et al., eds., *Recombinant DNA*, 2nd Ed., W. H. Freeman and Company, New York (1992), the entire disclosures of which are incorporated herein by reference.

In certain embodiments, the target molecules are mutated human nucleotide sequences which represent somatic cell mutations associated with cancers. For example, and without limitation, nucleotide sequences characteristic of colon cancer can be identified in feces, sequences characteristic of renal or bladder cancer can be identified in urine, sequences characteristic of retinoblastomas can be identified in vitreous humor, sequences characteristic of gliomas or neuroblastomas can be identified in cerebrospinal fluid, and sequences characteristic of breast cancer can be identified in mammary or axillary biopsies.

In other embodiments, the target molecules are allelic variants of human nucleotide sequences which are associated with genetic predispositions to disease or which are useful for forensic identification of individuals. For example, and without limitation, nucleotide sequences characteristic of predispositions to certain cancers can be identified in feces, blood or biopsy samples, sequences characteristic of specific individuals can be identified from blood, saliva, and semen samples obtained in criminal investigations; and sequences characteristic of specific haplotypes can be identified from amniotic fluid, or fetal or neonatal samples for paternity testing.

In other embodiments, the target molecules are pathogen-derived nucleic acids or proteins present in a test sample from an infected human subject. For example, and without limitation, nucleic acids or proteins characteristic of HIV-infection can be identified in a blood or plasma sample; nucleic acids or proteins characteristic of *Pseudomonas aeruginosa* or *Mycobacterium tuberculosis* infection can be identified in a sputum sample; or nucleic acids or proteins characteristic of infection with a sexually-transmitted disease can be identified in a semen sample.

In other embodiments, the target molecules are pathogen-derived nucleic acids or proteins present in a test sample from an environmental, industrial or commercial sample. For example, and without limitation, nucleic acids or proteins characteristic of HIV-infection can be identified in a sample from a blood or organ bank; nucleic acids or proteins characteristic of *Salmonella enteriditis* or *Escherichia coli* serotype 01 57:H7 contamination can be detected in food processing facilities; or proteins characteristic of *Vibrio cholerae* or coliform bacteria can be identified in water supplies.

Binding Partners

In some embodiments, the binding partner is a polynucleotide, an antibody, an aptamer, a receptor or a ligand. In each instance, the probe can be a naturally occurring molecule which is modified only to facilitate immobilization within the electrophoretic medium or for ease of detection, or can be a genetically or chemically engineered molecule which is modified for purposes of increased, decreased or altered selective binding affinity; increased, decreased or altered chemical or thermal stability; or other altered characteristics useful for the intended purpose.

The polynucleotide probes can be DNA probes, RNA probes, or polynucleotide probes having modified nucleoside bases or modified internucleoside linkages, whether known in the art or yet to be developed. Examples of modified nucleoside bases include, without limitation, the modified bases described in WIPO Standard ST.25 (1998), Appendix 2, Table 2, the entire disclosure of which is incorporated by reference herein (see also 37 C.F.R. 1.821-1.825). Examples of modified internucleoside linkages include, without limitation, modifications of the ribosyl or deoxyribosyl units such as halogenation, alkylation, alkoxylation or the like (e.g., 2-fluorination, 2-0-methylation, 5-methylation), modification or replacement of the phosphodiester linkages (e.g., substitution with phosphorothioate linkages), or modification or replacement of both the (de-oxy)ribosyl and phosphate backbone (e.g., substitution with peptide nucleic acid (PNA) linkages). See, for example, Wetmur (1991), *Crit. Rev. Biochem. Mol. Biol.* 26:227-259; Moody et al. (1989), *Nucleic Acids Res.* 17:4769-4782; Iyer et al. (1995), *J. Biol. Chem.* 270:14712-14717; Nielsen et al. (1991), *Science* 254:1497-1500.

In some embodiments, a polynucleotide probe has a length of between 15 and 200 bases. In certain embodiments, the polynucleotide probe has a length between 15 and 50 bases, between 50 and 80 bases, between 80 and 110 bases, between 110 and 140 bases, between 140 and 170 bases, or between 170 and 200 bases. Substantially longer binding partners also can be used.

Polynucleotide binding partners can be directed to sequences known to include nucleotide substitutions (including single nucleotide polymorphisms), deletions or insertions, or regions of microsatellite instability. For example, polynucleotide binding partners useful in the invention include, without limitation, those developed for the detection of BAT-26 sequences (see, e.g., U.S. Pat. No. 6,503,718), p53 gene sequences (see, e.g., U.S. Pat. No. 5,527,676), MCC gene sequences (see, e.g., U.S. Pat. No. 5,330,892), APC gene sequences (see, e.g., U.S. Pat. No. 5,352,775; U.S. Pat. No. 6,503,718), DCC gene sequences (see, e.g., U.S. Pat. No. 5,532,108) and MET oncogene sequences (see, e.g., Li et al. (2003), *Gene Ther. Mol. Biol,* 7:99-102).

Antibody binding partners can include naturally occurring antibodies produced or isolated from animals or cell culture, including polyclonal or monoclonal antibodies. Alternatively, antibody binding partners can include genetically engineered molecules, including chimeric antibodies, produced in recombinant organisms or cells, or can be chemically engineered molecules produced by chemical syntheses or degradation (e.g., cleavage or digestion). Antibody binding partners useful in the invention also include antibody fragments, such as Fab fragments, F(ab')2 fragments, Fv fragments, or single-chain Fv fragments (scFv). Such antibody binding partners can be directed to epitopes known to include specific amino acid substitutions, deletions or insertions, or altered post-translational processing of proteins.

Antibodies may be produced by standard methods, well known in the art. See, e.g., Pluckthun, *Nature* 347:497-498 (1990); Huse et al, *Science* 246:1275-1289 (1989); Chaudhary et al., *Proc. Natl. Acad. Sci. USA* 87:1066-1070 (1990); Mullinax et al., *Proc. Natl. Acad. Sci. USA* 87:8095-8099 (1990); Berg et al., *Proc. Natl. Acad Sci. USA* 88:4723-4727 (1991); Wood et al., *J. Immunol.* 145:3011-3016 (1990); and references cited therein. Antibody binding partners useful in the invention include, without limitation, those specific for the detection of human carcinoma-associated antigens (see, e.g., PCT Intl. Pub. No. WO 96/08514), and prostate specific antigen (PSA).

Aptamer binding partners can be developed and selected by methods well known in the art (see, e.g., Tuerk et al. (1990), *Science.* 249:5050; Joyce (1989), *Gene* 82:83-87; Ellington et al. (1990), *Nature* 346:818-822; Klug et al. (1994), *Mol. Biol. Reports* 20:97-107), and can be used as binding partners against many kinds of analytes, including proteins, carbohydrates and small organic molecules.

Binding partners can be covalently bound to a region of the electrophoretic medium, can be bound to the medium ionically or by affinity binding, or can be trapped within the interstices of a medium comprising a cross-linked polymeric matrix.

A great variety of methods are known in the art for covalently binding partners such as polynucleotides or antibodies to various electrophoretic media. The methods can employ standard chemistries using reactive groups present on the binding partners and/or electrophoretic medium, or one or both of the binding partner and electrophoretic medium can be functionalized to add a desired reactive group. For example, and without limitation, carboxyl groups can be reacted with amine groups using carbodiimide conjugation reactions; primary amines can be reacted with other amine groups using glutaraldehyde; CNBr treatment can convert hydroxyl groups to cyanate ester or imidocarbonate groups which can be reacted with primary amines; and cyanuric chloride treatment can convert primary amines to chlorotriazines which can be reacted with primary amines or thiols. For a review of useful conjugation reactions, see, e.g., Wong, ed., *Chemistry of Protein Conjugation and Cross-Linking*, CRC Press, Boca Raton, Fla. (1993).

Alternatively, binding partners can be conjugated to one member of an affinity binding pair such that the probes can be immobilized within an electrophoretic medium through a binding partner which is bound to the medium. Affinity binding pairs useful in this context include, without limitation, the biotin and streptavidin binding pair and the digoxigenin and antidigoxigenin binding pair. Thus, for example, and without limitation, binding partners can be conjugated to biotin to cause immobilization of the binding partners on beads coated with avidin or streptavidin. A packed volume of such beads can constitute an electrophoretic medium, or the beads can be intermixed with a polymeric matrix or gel to form a hybrid gel-bead electrophoretic medium. See, for example, U.S. Pat. No. 5,482,863, which describes methods for casting electrophoretic gels containing suspensions or particles. For antibody binding partners, the antibody itself can serve as an affinity binding partner with Protein A, which can be immobilized within the electrophoretic medium (see, e.g., Surolia et al. (1981), *Trends Biochem. Sci.* 7:74). Alternatively, antibodies can be immobilized on Protein A-coated beads.

In other embodiments, binding partners can be functionalized with a monomer unit which is to be polymerized or co-polymerized to form an electrophoretic medium. When such modified binding partners are copolymerized with suitable mixtures of the monomers, polymeric media containing high concentrations of the immobilized binding partners can be produced. For example, and without limitation, binding partners functionalized with acrylamide groups (e.g., 5' acrylamide groups for polynucleotide binding partners) can be co-polymerized within a region of a polyacrylamide electrophoretic medium. Additional examples of methods for covalently attaching nucleic acids to polymerizable chemical groups are found in U.S. Pat. No. 5,932,711; U.S. Pat. No. 6,180,770; U.S. Pat. Appln. Pub. No. 2002/0172955; U.S. Pat. Appln. Pub. No. 2002/0197614 and PCT Intl. Pub. No. WO 98/51823. See also, Rehman et al. (1999), *Nucleic Acids Res.* 27:649; Bille et al. (1989), *Eur. J. Biochem.* 180:41-47; Wang et al. (1997), *Nature Biotechnology* 15:789-793; Holtz et al. (1997), *Nature* 389: 829-832; Timofeev et al. (1996), *Nucleic Acids Res.* 24:3142-3148; and U.S. Pat. No. 5,478,893 for descriptions of other methods that have been used to immobilize proteins and small organic molecules within polymeric matrices and gels.

Electrophoretic Apparatus

An apparatus for electrophoresis typically includes an electrophoretic medium disposed within a non-conductive housing and at least one pair of electrodes for applying an electric field across the medium in a spatial dimension defined by the electrodes. The housing typically contains and defines the shape of an electrophoretic medium in the form of a substantially planar gel or, in capillary electrophoresis, a cylinder or capillary tube. Other shapes and conformations, however, can be used in accordance with the invention. In two-dimensional electrophoresis, a second pair of electrodes defines a second spatial dimension across the medium. See, generally, Giddings, ed., *Unified Separation Science*, John Wiley & Sons, New York (1991), p. 155-170.

With a conventional two-electrode apparatus for one-dimensional electrophoresis, reversal of the electric field can be achieved simply by switching the polarity of the two electrodes, as practiced in field inversion gel electrophoresis (Carle et al (1986), *Science* 232:65-68). Two-dimensional electrode arrangements, as used in pulsed field electrophoresis (see, e.g., Schwartz et al. (1984), Cell 3 7:67), allow the separation process of the present invention to be performed in two spatial dimensions. In principle, the addition of another set of electrodes operating in a third spatial dimension could add additional separation capability if desired.

The state of instrumentation and methodology for performing one- and two-dimensional electrophoretic separations is well advanced. At least one commercially available device (CHEF® gel apparatus, Bio-Rad Life Science Research Products Catalog (1997), pp. 175-182) offers the capability of performing two-dimensional electrophoretic separations with programmable automated control of field orientation and pulse duration.

The present invention further provides an electrophoretic apparatus in which the electrophoretic medium includes at least two regions having distinct binding partners immobilized within each region. In some embodiments, the invention provides an electrophoretic apparatus or system in which the electrophoretic medium includes at least three regions having distinct binding partners immobilized within each region. In some embodiments comprising at least three regions, the binding partners in adjacent regions are distinct, but binding partners in non-adjacent regions can be the same.

The adjacent regions of the apparatus can be contiguous or can be separated by a void, spacer or separator that allows fluid communication between the regions. The apparatus can also include a sample inlet chamber to allow for introduction of a test sample, or a collection chamber to allow for removal of solvent and molecules which have eluted from the medium. The apparatus can also include means for regulating the temperature of the entire electrophoretic medium or discrete regions.

Figure 7:
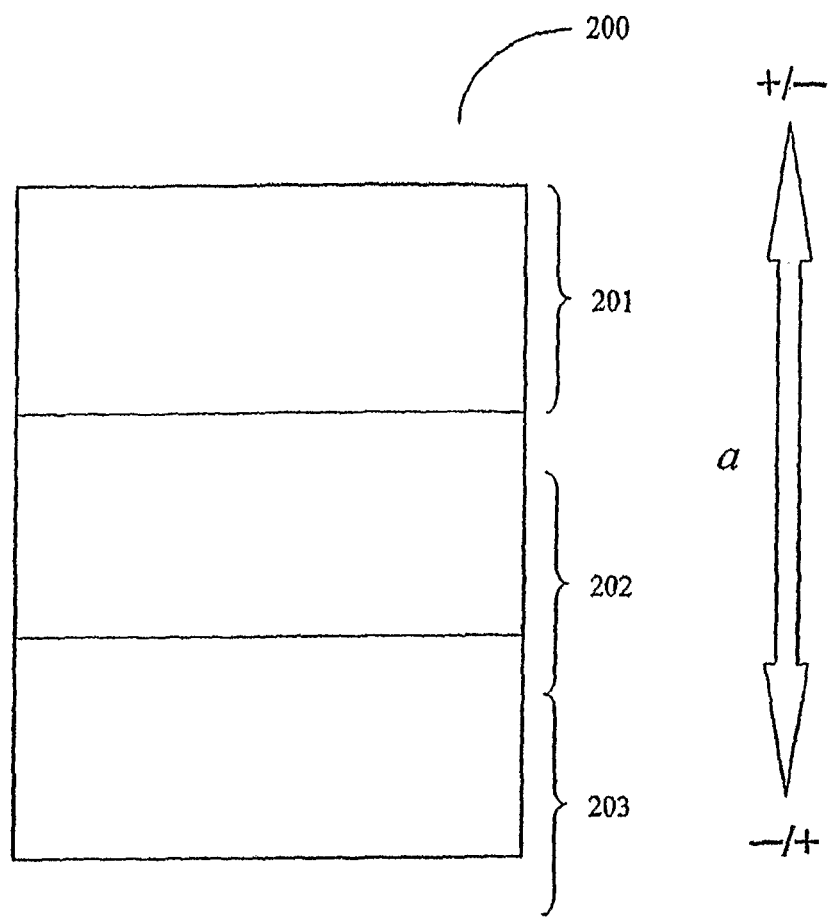
FIG. 7 is a schematic representation, of an electrophoretic device of the invention having an electrophoretic medium with three regions.

The apparatus can also include a detector for detecting a sample front (i.e., the line of furthest advance of the sample through the medium) as it approaches a distal edge of the electrophoretic medium. Referring to FIG. 7, for example, if a sample is applied or introduced to the first region 201, electrophoresis will cause charged molecules to migrate through the second region 202 and into the third region 203. The detector can detect the sample as it reaches the distal edge of the third region 203, and cause the electric field to be reversed, thereby reversing the direction of electrophoresis.

Another detector can be disposed at the opposite distal edge of first region 201 to detect the sample front as it returns and cause the electric field to reverse again, initiating another cycle of reversed field electrophoresis. A dye can be included in the test sample to facilitate detection by an optical detector. Alternatively, the detector can detect changes in resistance or conductivity caused by solutes in the sample. The apparatus can also include a timer for reversing the electric field periodically. For example, once the period of time necessary for the sample front to reach the distal edge of the electrophoretic medium is determined, a timer can be set to periodically reverse the electric field after the determined period, or after a somewhat shorter or longer period.

The apparatus can also include a counter for tracking the number of cycles of reversed-field electrophoresis. For example, the counter can record or register each reversal of the electric field, and the counter can be set to signal (e.g., audibly, visibly or electronically) when a predetermined number of cycles has been reached, or to terminate the repetitive reverse-field electrophoresis when a predetermined number of cycles has been reached.

Systems for Repetitive Reversed-Field Affinity Electrophoresis

The present invention also provides systems for repetitive reversed-field affinity electrophoresis. Such systems include an electrophoretic apparatus, such as those described above, as well as other elements that can be used in the methods. For example, the systems can include a non-conductive housing for containing the electrophoretic medium, one or more pairs of electrodes disposed within the housing for applying an electric field across the medium in one or more spatial dimensions, and the electrophoretic medium itself.

In some embodiments, the electrophoretic medium includes at least two regions arranged in one spatial dimension, whereas in other embodiments the medium includes three or more regions arranged in one or more spatial dimensions. In each embodiment, at least one of the regions includes binding partners having selective binding affinity for target molecules and, in certain embodiments, at least one of the regions includes binding partners having selective binding affinity for non-target molecules.

In some systems, the electrophoretic medium includes at least three regions arranged in one spatial dimension, and each of the regions includes binding partners immobilized in that region and differing from the binding partners in each immediately adjacent region. In certain embodiments, at least two non-adjacent regions have identical binding partners. Thus, for example, and without limitation, the first and third regions can include differing or identical binding partners for non-target molecules and the second region can include binding partners for target molecules.

Optionally, the systems can include a detector for detecting a sample front as it approaches an edge of the electrophoretic medium. In certain embodiments, the systems include means for reversing the electric field after the detector detects the sample front.

Optionally, the systems can include a counter for tracking the number of cycles of reversed-field electrophoresis. In certain embodiments, the systems include means for signaling when a predetermined number of cycles has been reached or for terminating the repetitive reverse-field affinity electrophoresis when a predetermined number of cycles has been reached.

In certain embodiments, the systems also include at least one separator, such as a mesh or semi-permeable membrane, that separates different regions of the electrophoretic medium. Such separators are particularly useful for separating regions including packed volumes of beads to prevent migration of the beads during electrophoresis. Thus, in certain embodiments, the system includes a separator adjacent to at least one region of the electrophoretic medium that includes a packed volume of beads.

Repetitive Affinity Separation

The present invention depends, in part, upon the discovery that the separation, isolation, enrichment or detection of target molecules within a sample is significantly improved by repetitively passing a sample across at least one region of a solid support or through or over at least one region of an electrophoretic medium that has a binding partner specific for the target molecule. In some embodiments, there are two or more regions including binding partners specific for different target molecules. In some embodiments, at least one other region includes a binding partner specific for non-target molecules.

Without being bound to any particular theory of the invention, it is believed that, as the sample moves across a binding partner region multiple times, target molecules within the sample have multiple opportunities to bind to the binding partners specific for the target molecules. Similarly, non-target molecules have multiple opportunities to bind to any binding partners specific for the non-target molecules. In addition, non-specifically bound molecules have additional time and opportunities to be displaced. In an embodiment, the sample is rapidly moved across the binding partner, selecting for only very high specificity binding. Moreover, as a result of the increased opportunities for specific binding, it is believed that that higher stringency binding conditions can be employed to achieve higher specificity without substantial loss of sensitivity. Therefore, the quality of the separation, isolation, enrichment or detection of target molecules is also significantly improved.

The methods are particularly useful for the separation, isolation, enrichment or detection of dilute or heterogeneous samples of biomolecules obtained from bodily fluids, excreta or tissue samples, and can be particularly useful in identifying human wild-type or mutant nucleotide sequences or pathogen-derived nucleotide sequences in stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin.

For example, such methods can be useful in the diagnosis or staging of cancers (e.g., detection of colon cancer-associated nucleic acids or proteins in stool samples), in the diagnosis of infectious disease (e.g., detection of viral proteins in blood samples), in prenatal genotyping (e.g., detection of fetal nucleic acids in amniotic fluid or maternal blood), as well as non-medical applications such as environmental testing (e.g., detection of pathogens in water supplies) and industrial or commercial process controls (e.g., meat and poultry processing; food and pharmaceutical processing).

Furthermore, the methods are particularly useful for separating, isolating, enriching or detecting multiple targets in a single sample. For example, a genomic DNA, mRNA, cDNA or amplified DNA sample can be screened for the presence a multiplicity of mutant or marker DNA sequences simultaneously, or an environmental sample can be screened for the presence of a multiplicity of pathogens simultaneously.

Repetitive Reverse-Field Affinity Electrophoresis

In an embodiment, the present invention provides methods for separating target molecules from non-target molecules in a test sample by subjecting the sample to repetitive reversed-field affinity electrophoresis in an electrophoretic medium having at least two regions arranged consecutively, e.g., in a first spatial dimension. At least one of the regions includes a first binding partner having selective binding affinity for a first target molecule and not having selective binding affinity the non-target molecules. The electrophoretic medium is first subjected to an electric field in a first direction resulting in migration within the medium of charged molecules amongst the regions in the first spatial dimension. The electric field is then reversed such that the electrophoretic medium is subjected an electric field in a second direction substantially antiparallel to the first direction, resulting in migration within the medium of charged molecules in the test sample amongst the regions in the first spatial dimension. This process of reversing the electric field and electrophoresing the sample in the opposite direction can be repeated one or more times. For example, the test sample can be subjected to 5, 10, 20, 30 or more cycles of reversed-field electrophoresis in which the sample is electrophoresed in one direction and then the opposite direction. In one embodiment, a test sample can be subjected to 14 cycles (e.g., 7 in each direction) of reversed-field electrophoresis. In an embodiment, the first and second electrophoretic fields comprise between about I Amps to about 200 Amps, depending upon the electrophoretic medium used (e.g., concentration of agarose or polyacrylamide, pH, temperature) and size of the molecule or cell being separated or isolated. In another embodiment, the first and second electrophoretic fields cause the target molecule to move through the medium at a rate of between about I mm/mm. to 30 about 100 cm/mm.

Figure 6:
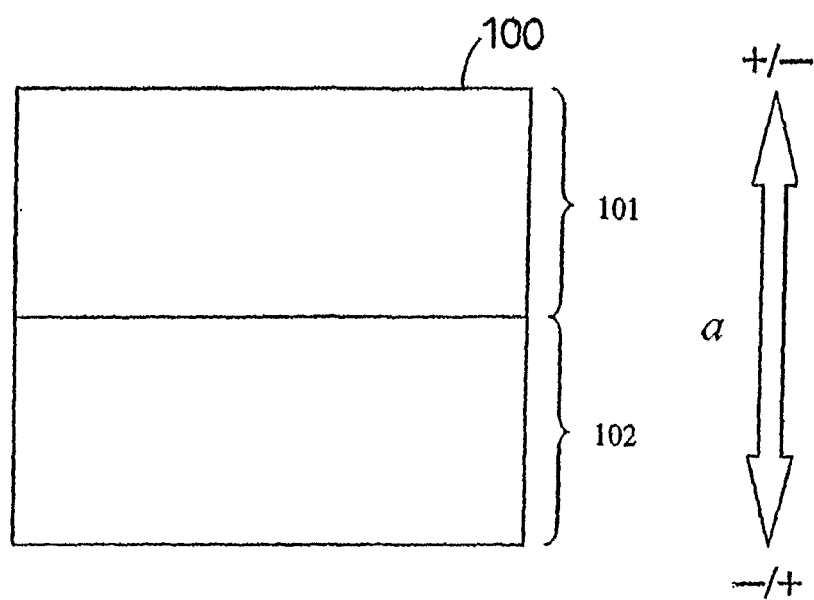
FIG. 6 is a schematic representation of an electrophoretic device of the invention having an electrophoretic medium with two regions.

FIG. 6 is a schematic representation of an electrophoretic device of the invention having an electrophoretic medium 100 with a first region 101 and a second region 102. In the foregoing embodiments, one region includes immobilized target-specific binding partners and the other does not. These regions are arranged in a first spatial dimension indicated by arrow a. The test sample is applied or introduced to one or both regions, typically to the distal edge of one region, and is then subjected to an electric field in dimension a such that charged molecules migrate amongst the regions. The electric field is then reversed such that charged molecules migrate amongst the regions in the opposite direction in dimension a. In accordance with the invention, the electric field can be reversed and the test sample can be electrophoresed forward and backward multiple times in spatial dimension a to achieve improved separation. The regions need not be of equal size as shown in the schematic representation of FIG. 6, and the shapes of the regions can be arbitrary. Furthermore, the binding partners need not be evenly distributed within a region.

FIG. 7 is a schematic representation of an electrophoretic device of the invention having an electrophoretic medium 200 with a first region 201, a second region 202 and a third region 203. In the foregoing embodiments, one region (e.g., the second region 202) includes immobilized target-specific binding partners. These regions are arranged in a first spatial dimension indicated by arrow a. The test sample is applied or introduced to one or more regions, typically to the distal edge of region 201 or 203, and is then subjected to an electric field in spatial dimension a such that charged molecules migrate amongst the regions. The electric field is then reversed such that charged molecules migrate amongst the regions in the opposite direction in spatial dimension a. In accordance with the invention, the electric field can be reversed and the test sample can be electrophoresed back-and-forth multiple times in spatial dimension a to achieve improved separation. In some embodiments, the electrophoretic medium has a second region that includes second target binding partners having selective binding affinity for second target molecules and not having selective binding affinity for non-target molecules. In these embodiments the second target molecules are different from the first target molecules, and the second target molecules are selectively bound to the second target 30 binding partners and separated from non-target molecules in the test sample.

Referring again to FIG. 6, an electrophoretic device of the invention has an electrophoretic medium 100 with a first region 101 and a second region 102, arranged in a first spatial dimension indicated by arrow a. In these embodiments, the first region 101 includes first target binding partners and the second region 102 includes second target binding partners. Similarly, referring again to FIG. 7, an electrophoretic device of the invention has an electrophoretic medium 200 with a first region 201, a second region 202 and a third region 203, arranged in a first spatial dimension indicated by arrow a. In these embodiments, two regions e.g., the first region 201 and second region 202) include first and second target binding partners. As before, the test sample is applied or introduced to one or more of the regions, and is subjected to repetitive reversed-field electrophoresis in dimension d. In other embodiments, the electrophoretic medium has a multiplicity of regions arranged consecutively in the first spatial dimension, and each such region includes different target binding partners having selective binding affinity for different target molecules and not having selective binding affinity for non-target molecules. In these embodiments, a multiplicity of different target molecules are selectively bound to the multiplicity of target binding partners and separated from non-target molecules in the test sample. In certain embodiments, there are 5-10, 5-50, 5-100 or more different regions including different target binding partners.

In another embodiment, an electrophoretic device of the invention has an electrophoretic medium with a first region, a second region, a third region and a fourth region. A multiplicity of regions include immobilized target-specific binding partners. Optionally, one or more regions that does not include target-specific binding partners does include non-target-specific binding partners. The regions are arranged in a first spatial dimension. As before, the test sample is applied or introduced to one or more of the regions, and is subjected to repetitive reversed-field electrophoresis in a dimension.

In another aspect, the present invention provides methods employing both target-specific and non-target-specific binding partners. In these embodiments, at least one of the regions arranged in the first spatial dimension of the electrophoretic medium includes target binding partners having selective binding affinity for target molecules and not having selective binding affinity for non-target molecules, and at least one of the regions includes non-target binding partners having selective binding affinity for at least some non-target molecules and not having selective binding affinity for target molecules. The region including the non-target-specific binding partners is useful for removing at least some non-target molecules from the electrophoretically migrating sample, thereby eliminating some non-target molecules which might non-specifically bind to target-specific binding partners or otherwise interfere with the binding of target molecules to target-specific binding partners. As in the previously described embodiments, the test sample is applied or introduced to one or more of the regions, and is subjected to repetitive reversed-field electrophoresis in the first spatial dimension.

Referring again to FIG. 6, an electrophoretic device of the invention has an electrophoretic medium 100 with a first region 101 and a second region 102, arranged in a first spatial dimension indicated by arrow a. In these embodiments, the first region 101 includes target-specific target binding partners and the second region 102 includes non-target-specific binding partners. Similarly, referring again to FIG. 7, an electrophoretic device of the invention has an electrophoretic medium 200 with a first region 201, a second region 202 and a third region 203, arranged in a first spatial dimension indicated by arrow a. In these embodiments, at least one region includes target-specific binding partners (e.g., the second region 202) and at least one region includes non-target-specific binding partners (e.g., the first region 201 and/or the third region 203). Similarly, in one embodiment, an electrophoretic device of the invention has an electrophoretic medium with a first region, a second region, a third region, and a fourth region, arranged in a first spatial dimension. In these embodiments, at least one region includes target-specific binding partners (e.g., the second region and the third region) and at least one region includes non-target-specific binding partners (e.g., the first region and/or the fourth region). As before, the test sample is applied or introduced to one or more of the regions, and is subjected to repetitive reversed-field electrophoresis in a dimension.

In some embodiments of each of the foregoing aspects, the electrophoretic medium further includes at least one perpendicular region which is adjacent to at least one of the other regions in a second spatial dimension substantially perpendicular to the first spatial dimension. In these embodiments, the method includes the additional step of subjecting the electrophoretic medium to an electric field in a third direction parallel to the second spatial dimension, resulting in migration within the electrophoretic medium of charged molecules in the test sample amongst the regions in the second spatial dimension. Thus, the invention provides for separation in a second spatial dimension. In some embodiments, the perpendicular region includes binding partners having selective binding affinity for at least some molecules in the sample. In accordance with the invention, the electric field in the second spatial dimension optionally can be reversed and the test sample can be electrophoresed back-and-forth multiple times in the second spatial dimension to achieve improved separation. Electrophoresis in the second spatial dimension can be performed before, after or alternately with electrophoresis in the first spatial dimension. In some embodiments, electrophoresis in the second spatial dimension is performed only once, without field-reversal, to achieve a final separation prior to isolation or detection of the target molecules.

Figure 8:
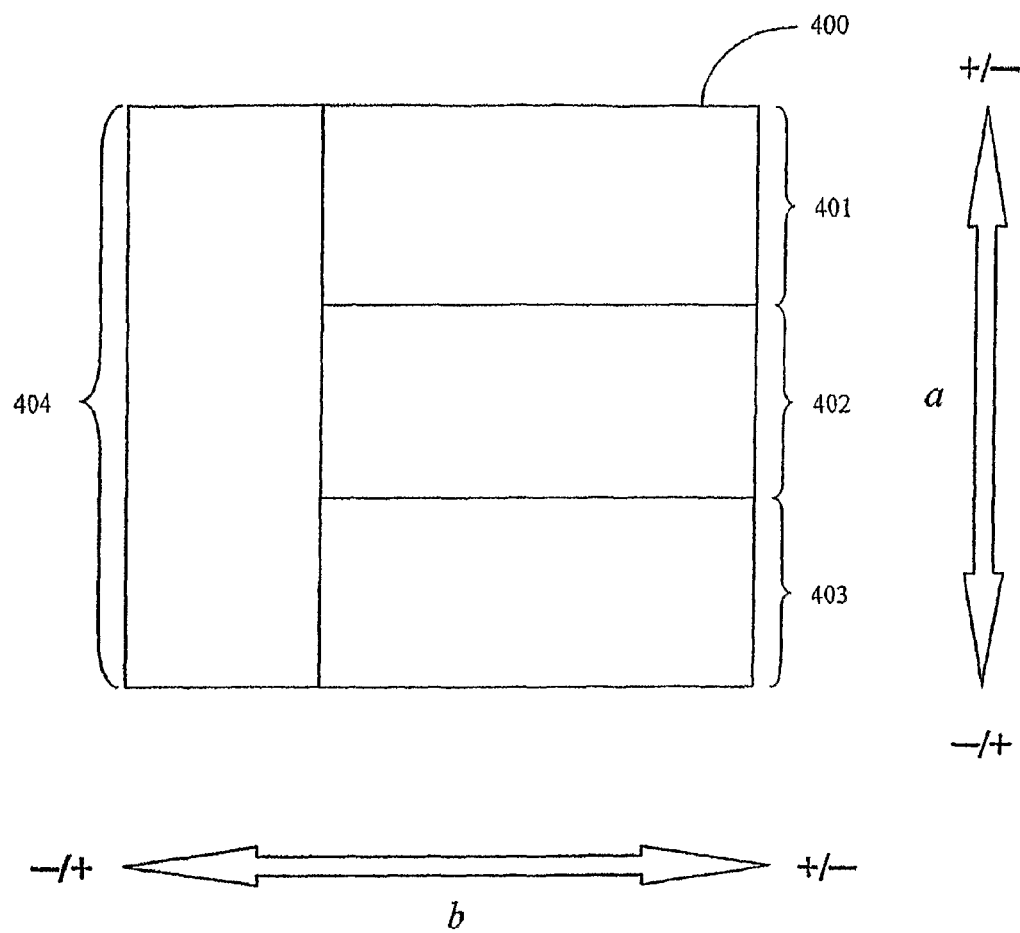
FIG. 8 is a schematic representation of an electrophoretic device of the invention having an electrophoretic medium with four regions arranged in two spatial dimensions.

FIG. 8 is a schematic representation of an electrophoretic device of the invention having an electrophoretic medium 400 with a first region 401, a second region 402, and a third region 403 arranged in a first spatial dimension indicated by arrow a-A perpendicular region 404 is arranged in a second spatial dimension indicated by arrow b relative to the other regions. At least one of regions 401, 402 and 403 includes immobilized target-specific binding partners. Optionally, one or more of regions 401, 402 and 403 which does not include target-specific binding partners can include non-target-specific binding partners. The perpendicular region 404 can optionally include target-specific or non-target-specific binding partners. The test sample is applied or introduced to one or more regions, typically to the distal edge of region 401 or 403, and is then subjected to an electric field in spatial dimension a such that charged molecules migrate amongst regions 401, 402 and 403. The electric field is then reversed such that charged molecules migrate amongst these regions in the opposite direction in spatial dimension a. In accordance with the invention, the electric field can be reversed and the test sample can be electrophoresed back-and-forth multiple times in spatial dimension a to achieve improved separation. The test sample is also subjected to an electric field in spatial dimension b such that charged molecules migrate amongst regions 401, 402 and 403 and perpendicular region 404. The electric field can be reversed and the sample can be electrophoresed back-and-forth multiple times in spatial dimension b, or electrophoresis in dimension b can be performed only once, without field-reversal, to achieve a final separation prior to isolation or detection of the target molecules. Although three regions (i.e., 401, 402 and 403) are shown in spatial dimension, an arbitrary number of regions can be included. Similarly, additional regions can be included in spatial dimension b.

In another aspect, the invention provides methods of isolating target molecules (e.g. nucleic acids) from non-target molecules in a test sample. In these methods, the target molecules are separated by any of the methods described above, and then the target molecules are released by treating the electrophoretic medium to release either the target molecules from target-specific binding partners, or to release complexes of the target molecules and target-specific binding partners. These released molecules are then eluted from the electrophoretic medium to isolate the target molecules. The treatment for releasing the molecules depends upon the nature of the molecules to be released. For example, and without limitation, heat, salts, denaturants, or increased electric fields can be used to release polypeptides or proteins bound to polypeptide, protein or aptamer binding partners, or to dissociate nucleic acid targets hybridized to complementary or substantially complementary polynucleotide binding partners. Similarly, and without limitation, chemical cleavage, enzymatic cleavage, or mechanical cleavage (e.g., cutting the binding region from the medium), as well as heat, salts, denaturants, or increased electric fields, can be used to release complexes of immobilized binding partners and bound target molecules from the medium.

In another aspect, the invention provides methods of enriching for target molecules (e.g., specific nucleic acids) relative to non-target molecules in a test sample. In these methods, the target molecules are separated and released by any of the methods described above, and then the target molecules are eluted from the electrophoretic medium to provide a sample enriched for the target molecules.

In another aspect, the invention provides methods of detecting target molecules (e.g., specific nucleic acids) in a test sample containing non-target molecules. In these methods, the target molecules are separated by any of the methods described above, optionally isolating or enriching for the target molecules by the methods described above, and then the target molecules are detected by any appropriate method of detection. For example, and without limitation, polypeptide target molecules can be detected by binding of a detectable antibody, aptamer, receptor or ligand specific for the target polypeptide, and nucleic acid target molecules can be detected by binding of a polynucleotide probe specific for the target nucleic acid, or by displacement of a detectable polynucleotide hybridized to target-specific binding partners by the target nucleic acids. Optionally, target molecules which are nucleic acids can be amplified prior to detection.

In some of the foregoing embodiments, the adjacent regions of the electrophoretic medium are contiguous such that the regions form a single continuous electrophoretic medium. In other embodiments, the regions are not contiguous but, rather, are separated either by a solvent-filled void, spacer, separator, or other structure(s) such that the regions form a discontinuous electrophoretic medium in which the regions are in fluid communication. In embodiments employing packed volumes of beads in one or more regions of the electrophoretic medium, separators can prevent beads from migrating amongst regions in response to an electric field.

In some of the foregoing embodiments, the invention is employed with highly heterogeneous or complex test samples in which the target molecules comprises a very small fraction of the biomolecules present. In some of these embodiments, it is contemplated that the invention can employ (a) a greater number of non-target specific binding partners relative to target-specific binding partners to capture the greater relative number of non-target molecules, (b) a variety of non-target specific binding partners to capture a variety of non-target molecules, and/or (c) non-target specific binding partners with less specificity or selectivity relative to target-specific binding partners such that each non-target specific binding partner can capture a variety of different non-target molecules (e.g., under a given set of conditions, longer polynucleotide probes can hybridize with lower specificity than shorter probes).

In some of the foregoing embodiments, the adjacent regions of the electrophoretic medium are identical except for the differing binding partners immobilized within the different regions. In other embodiments, the regions can differ in the chemical composition of the medium such that characteristics such as pore size, denaturant composition and/or concentration, ionic charge, pH, salt concentration, or hydrophobicity/hydrophilicity are varied. Such variables can be used to separate molecules based upon physical size in native or denatured conformations, net charge at different pH values, binding affinity for binding partners at different binding (e.g., hybridization) stringencies, or non-specific binding affinity for the electrophoretic medium itself. These characteristics can also be varied within a region over time by varying the electrophoresis solvent or otherwise treating the region. Finally, the temperature of the electrophoretic medium and the strength of the electric field can be varied over time, thereby affecting the binding characteristics of the binding partners immobilized within the different regions of the electrophoretic medium.

It is understood by those of skill in the art that the separation, isolation or enrichment of a target molecule in a sample need not be complete for most analytical or diagnostic purposes. Rather, varying degrees of separation, isolation or enrichment have utility for varying purposes. Therefore, the terms "separation", "isolation" or "enrichment" are intended to have their usual meaning in the art, conveying a statistically significant increase in separation, isolation or enrichment and not an absolute separation of all target molecules from all non-target molecules.

I claim:

1. A method of detecting an altered or mutant nucleic acid molecule that is present in a target nucleic acid in a biological sample at a frequency that is suspected to be one percent or lower, wherein the presence of the altered or mutant nucleic acid is known to be indicative of an adenoma, early stage cancer, or infection with HIV, *Pseudomonas aeruginosa, Mycobacterium tuberculosis*, or a sexually transmitted disease, comprising:

(a) reducing the genomic complexity of the biological sample by repeatedly exposing at least 100/x genome equivalents of the target nucleic acid from the biological sample to a capture probe specific for the target nucleic acid via application of an electric field using electrophoretic methods to capture the 100/x genome equivalents of the target nucleic acid, wherein x percent is the suspected frequency of the altered or mutant nucleic acid present in the copies of the target nucleic acid and x is about 1.0 or less, and wherein the at least 100/x genome equivalents of target nucleic acid are captured from the biological sample; and (b) analyzing the at least 100/x genome equivalents of captured nucleic acid from step (a), wherein the captured nucleic acid comprises mutant or altered nucleic acid and normal nucleic acid molecules of the target nucleic acid, using a single molecule sequencing technique, wherein the analyzing detects the presence or absence of the altered or mutant nucleic acid molecule of the target nucleic acid at the frequency of x percent of the total genome equivalents captured from the biological sample, and wherein both step (a) and step (b) are performed without amplification.

2. The method of claim 1, wherein the biological sample is stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid harvested from a mucosal surface, hair, or skin.

3. The method of claim 1, wherein the mutant or altered nucleic acid molecule of the target nucleic acid is suspected to be present in the biological sample at a frequency of about 0.0001%, about 0.001%, about 0.01%, about 0.1%, or about 1.0% and at least 1,000,000, at least 100,000, at least 10,000, at least 1,000, or at least 100 genome equivalents, respectively, are captured and analyzed.

4. The method of claim 1, wherein the target nucleic acid molecules are at least 70 base pairs long.

5. The method of claim 1, wherein the target nucleic acid molecules are at least 200 base pairs long.

6. The method of claim 1, wherein each genome equivalent of the target nucleic acid is sequenced.

7. The method of claim 6, wherein a portion of each genome equivalent of the target nucleic acid is sequenced.

8. The method of claim 6 or 7, wherein the single molecule sequencing technique is used to obtain sequence information for each genome equivalent of the target nucleic acid.

9. The method of claim 1, wherein the capture probe is immobilized on a solid support or in a medium.

10. The method of claim 1, wherein repeated exposure to the capture probe is by repetitive reversed-field affinity electrophoresis.

11. The method of claim 10, wherein the repetitive reversed-field affinity electrophoresis is performed in an electrophoretic medium having at least two regions arranged consecutively, wherein at least one region includes an immobilized target-specific binding partner and wherein at least one region does not include an immobilized target-specific binding partner.

12. The method of claim 11, wherein at least one of the at least two regions includes an immobilized non-target-specific binding partner.

13. The method of claim 11, wherein the at least two regions are fluidically isolated.

14. A method of detecting two or more altered or mutant nucleic acid molecules that are present in the copies of two or more target nucleic acids in a biological sample at a frequency that each is suspected to be one percent or lower in a biological sample in a single assay, wherein the presence of two or more mutant or altered nucleic acid molecules is indicative of an adenoma, early stage cancer, or infection with HIV, *Pseudomonas aeruginosa, Mycobacterium tuberculosis*, or a sexually transmitted disease, comprising:

(a) reducing the genomic complexity of the biological sample by repeatedly exposing at least 100/x genome equivalents for each target nucleic acid from the biological sample to a capture probe specific for each target nucleic acid via application of an electric field using electrophoretic methods to capture the 100/x genome equivalents of the target nucleic acid, wherein x percent is the suspected frequency of the each altered or mutant nucleic acid present in the copies of the each target nucleic acid, and x is about 1.0 or less and wherein the at least 100/x genome equivalents of each individual target nucleic acid are captured from the biological sample; and (b) analyzing the at least 100/x genome equivalents of captured nucleic acid from step (a), wherein the captured nucleic acid comprises mutant or altered nucleic acid and normal nucleic acid molecules of each target nucleic acid, using a single molecule sequencing technique, wherein the analyzing detects the presence or absence of the altered or mutant nucleic acid molecule of each target nucleic acid at the frequency of x percent of the total genome equivalents captured from the biological sample; and wherein both step (a) and step (b) are performed without amplification.

15. The method of claim 14, wherein at least one capture probe is immobilized on a solid support or in a medium.

16. The method of claim 14, wherein repeated exposure to the capture probe is by repetitive reversed-field affinity electrophoresis.

17. The method of claim 14, wherein the mutant or altered nucleic acid molecule is suspected to be present in the biological sample at a frequency of about 0.0001%, about 0.001%, about 0.01%, about 0.1%, or about 1.0%, and at least 1,000,000, at least 100,000, at least 10,000, at least 1,000, or at least 100 genome equivalents, respectively, are captured and analyzed.

18. The method of claim 14, wherein the target nucleic acid molecules are at least 70 base pairs long.

19. The method of claim 14, wherein the target nucleic acid molecules are at least 200 base pairs long.

20. The method of claim 14, wherein each genome equivalent of the target nucleic acid is sequenced.

21. The method of claim 14, wherein a portion of each genome equivalent of the target nucleic acid is sequenced.

22. A method of detecting an altered or mutant nucleic acid molecule that is present in the copies of a target nucleic acid in a biological sample at a frequency that is suspected to be one percent or lower, wherein the presence of the altered or mutant nucleic acid is known to be indicative of a disease, comprising:

(a) reducing the genomic complexity of the biological sample by repeatedly exposing at least 100 genome equivalents of the target nucleic acid from the biological sample to a capture probe specific for the target nucleic acid via application of an electric field using electrophoretic methods to capture the at least 100 genome equivalents of the target nucleic acid; and (b) analyzing the at least 100 genome equivalents of captured nucleic acid from step (a), wherein the captured nucleic acid comprises altered or mutant nucleic acid and normal nucleic acid molecules of the target nucleic acid, using a single molecule sequencing technique, wherein the analyzing detects the presence or absence of the altered or mutant nucleic acid molecule of the target nucleic acid at the frequency of one percent or lower of the total genome equivalents captured from the biological sample, and wherein both step (a) and step (b) are performed without amplification.

* * * * *